United States Patent
Morriss et al.

(10) Patent No.: US 9,867,972 B2
(45) Date of Patent: Jan. 16, 2018

(54) DELIVERY DEVICES FOR NASOPHARYNGEAL MUCOSA TARGETS

(71) Applicant: The Foundry, LLC, Menlo Park, CA (US)

(72) Inventors: John Morriss, San Francisco, CA (US); Hanson Gifford, Woodside, CA (US)

(73) Assignee: The Foundry, LLC, Menlo Park, CA (US)

(*) Notice: Subject to any disclaimer, the term of this patent is extended or adjusted under 35 U.S.C. 154(b) by 735 days.

(21) Appl. No.: 14/151,588

(22) Filed: Jan. 9, 2014

(65) Prior Publication Data
US 2014/0243793 A1    Aug. 28, 2014

Related U.S. Application Data

(63) Continuation of application No. PCT/US2012/046258, filed on Jul. 11, 2012.
(Continued)

(51) Int. Cl.
*A61M 31/00* (2006.01)
*A61M 15/08* (2006.01)
(Continued)

(52) U.S. Cl.
CPC ....... *A61M 31/007* (2013.01); *A61K 38/4893* (2013.01); *A61M 11/001* (2014.02);
(Continued)

(58) Field of Classification Search
CPC .. A61B 17/24; A61K 38/4893; A61K 9/0043; A61K 2039/543; A61M 15/08;
(Continued)

(56) References Cited

U.S. PATENT DOCUMENTS 2,490,168 A    12/1949  Strauss
3,948,254 A *  4/1976  Zaffaroni ............ A61M 31/002
                                                         128/833
(Continued)

OTHER PUBLICATIONS

European search report and search opinion dated May 6, 2015 for EP Application No. 12811642.3.
(Continued)

*Primary Examiner* — Gerald Landry, II
(74) *Attorney, Agent, or Firm* — Wilson Sonsini Goodrich & Rosati

(57) ABSTRACT

A system for delivering a therapeutic agent to nasopharyngeal mucosa tissue has a shaft, a porous pad of compliant material coupled to the shaft near the distal end, and a drug reservoir. The porous pad is configured to expand from a contracted configuration to an expanded configuration. The expanded configuration is adapted to engage and conform to the mucosa tissue in a nasal cavity, and the contracted configuration has a size suitable for introduction into the nasal cavity. The drug reservoir holds a therapeutic agent and is at least partially covered by the porous pad. The drug reservoir is configured to release a fixed volume of the therapeutic agent into the porous pad within a period of less than about 120 minutes, and has a wall with a plurality of channels fluidly coupled with the porous pad.

36 Claims, 20 Drawing Sheets

Related U.S. Application Data

(60) Provisional application No. 61/507,422, filed on Jul. 13, 2011.

(51) Int. Cl.
*A61M 11/00* (2006.01)
*A61K 38/48* (2006.01)
*A61M 16/04* (2006.01)
*A61M 11/06* (2006.01)
*A61M 5/32* (2006.01)

(52) U.S. Cl.
CPC .......... *A61M 11/007* (2014.02); *A61M 15/08* (2013.01); *A61M 15/085* (2014.02); *A61M 16/0438* (2014.02); *A61M 16/0461* (2013.01); *A61M 16/0481* (2014.02); *A61M 31/002* (2013.01); *A61M 5/329* (2013.01); *A61M 11/06* (2013.01); *A61M 2210/0618* (2013.01); *A61M 2210/0681* (2013.01)

(58) Field of Classification Search
CPC .......... A61M 2210/0618; A61M 31/00; A61M 31/002
USPC ................ 424/236.1, 434; 604/11, 285, 514; 606/196
See application file for complete search history.

(56) References Cited

U.S. PATENT DOCUMENTS

| | | | | |
|---|---|---|---|---|
| 3,993,072 | A * | 11/1976 | Zaffaroni | A61M 31/002 128/833 |
| 4,320,759 | A * | 3/1982 | Theeuwes | A61M 31/002 424/424 |
| 4,450,198 | A | 5/1984 | Michaels | |
| 5,011,474 | A * | 4/1991 | Brennan | A61B 17/12104 604/540 |
| 5,505,193 | A * | 4/1996 | Ballini | A61H 35/04 128/200.14 |
| 5,512,055 | A * | 4/1996 | Domb | A61K 9/0024 128/207.14 |
| 5,766,605 | A | 6/1998 | Sanders et al. | |
| 5,827,224 | A | 10/1998 | Shippert | |
| 6,123,697 | A * | 9/2000 | Shippert | A61B 17/12022 604/104 |
| 6,358,231 | B1 * | 3/2002 | Schindler | A61F 11/00 604/1 |
| 6,974,578 | B1 | 12/2005 | Aoki et al. | |
| 7,500,971 | B2 * | 3/2009 | Chang | A61B 34/20 604/510 |
| 8,696,227 | B1 * | 4/2014 | Carter | A61M 35/006 401/132 |
| 2003/0185872 | A1 * | 10/2003 | Kochinke | A61F 2/02 424/426 |
| 2004/0116958 | A1 | 6/2004 | Gopferich et al. | |
| 2005/0245906 | A1 * | 11/2005 | Makower | A61B 5/06 604/891.1 |
| 2005/0281751 | A1 * | 12/2005 | Levin | A61K 31/00 424/45 |
| 2006/0106361 | A1 * | 5/2006 | Muni | A61B 5/06 604/500 |
| 2006/0210605 | A1 * | 9/2006 | Chang | A61B 17/24 424/434 |
| 2007/0119451 | A1 * | 5/2007 | Wang | A61M 15/0028 128/203.15 |
| 2007/0129751 | A1 * | 6/2007 | Muni | A61B 17/24 606/196 |
| 2007/0267011 | A1 * | 11/2007 | Deem | A61M 29/02 128/200.23 |
| 2008/0015540 | A1 * | 1/2008 | Muni | A61B 17/24 604/500 |
| 2008/0097515 | A1 * | 4/2008 | Chang | A61B 34/20 606/196 |
| 2008/0132938 | A1 * | 6/2008 | Chang | A61B 90/16 606/196 |
| 2008/0215002 | A1 * | 9/2008 | Rozenberg | A61F 7/123 604/113 |
| 2008/0289629 | A1 | 11/2008 | Djupesland et al. | |
| 2009/0306624 | A1 * | 12/2009 | Arensdorf | A61K 9/0043 604/506 |
| 2010/0114066 | A1 * | 5/2010 | Makower | A61B 5/06 604/514 |
| 2010/0174278 | A1 * | 7/2010 | Barbut | A61F 7/123 606/21 |
| 2010/0198191 | A1 * | 8/2010 | Clifford | A61B 1/227 604/514 |
| 2010/0274164 | A1 * | 10/2010 | Juto | A61H 9/0078 601/46 |
| 2010/0282246 | A1 | 11/2010 | Djupesland et al. | |
| 2011/0004196 | A1 * | 1/2011 | Eaton | A61K 9/0024 604/514 |
| 2011/0066172 | A1 * | 3/2011 | Silverstein | A61F 11/006 606/162 |
| 2011/0088691 | A1 | 4/2011 | Djupesland | |
| 2011/0318345 | A1 * | 12/2011 | Djupesland | A61K 9/0043 424/134.1 |
| 2012/0000460 | A1 | 1/2012 | Flickinger | |
| 2012/0010698 | A1 * | 1/2012 | Hwang | A61F 2/82 623/1.42 |

OTHER PUBLICATIONS

International search report and written opinion dated Dec. 6, 2012 for PCT/US2012/046258.

Shaari, et al. Rhinorrhea is decreased in dogs after nasal application of botulinum toxin. Otolaryngol Head Neck Surg. Apr. 1995;112(4):566-71.

Unal, et al. Effect of botulinum toxin type A on nasal symptoms in patients with allergic rhinitis: a double-blind, placebo-controlled clinical trial. Acta Otolaryngol. Dec. 2003;123(9):1060-3.

\* cited by examiner

DELIVERY DEVICES FOR NASOPHARYNGEAL MUCOSA TARGETS

CROSS-REFERENCES TO RELATED APPLICATIONS

The present application is a continuation of International PCT Application No. PCT/US2012/046258, filed Jul. 11, 2012, which is a PCT of, and claims the benefit of U.S. Provisional Patent Application No. 61/507,422 filed Jul. 13, 2011; the entire contents of which are incorporated herein by reference.

This application is related to U.S. patent application Ser. No. 11/750,967 filed May 18, 2008, the entire contents of which are incorporated herein by reference. The present application is also related to U.S. Provisional Patent Application No. 61/507,417 filed Jul. 13, 2011, the entire contents of which are incorporated herein by reference.

BACKGROUND OF THE INVENTION

1. Field of the invention

The present disclosure relates generally to medical methods and delivery systems. More particularly, the present disclosure relates to methods and systems for delivering therapeutic agents such as toxins or non-toxins to mucosa targets in a nasopharyngeal space.

Rhinitis is commonly referred to as "stuffy nose," and results from inflammation and swelling of the mucus membranes lining the nasal cavity. Rhinitis falls into two major categories—allergic and non-allergic (or vasomotor). Chronic rhinitis can result in chronic inflammation of the nasal passages resulting in sinusitis, an infection or inflammation of the paranasal sinuses. Rhinitis includes the symptoms of rhinorrhea which is commonly referred to as "runny nose." Rhinorrhea describes the effluence of mucus from the lining of the nasal passages, nasopharynx, or paranasal sinuses. Rhinorrhea can be a symptom of a number of diseases such as the common cold, or sinusitis.

Allergic rhinitis is an immunologic response modulated by immunoglobulin E (IgE) and characterized predominantly by sneezing, rhinorrhea, nasal congestion, and pruritus of the nose. It may be seasonal (a condition commonly referred to as hay fever) or perennial. The seasonal form is caused by allergens released during tree, grass, or weed pollination, whereas the perennial form is caused by allergies to animal dander, dust mites, or mold spores with or without associated pollinosis. Data also suggest that urban air pollutants from automobiles and other sources may have an adjunctive effect.

Non-allergic rhinitis may be caused by anatomic pathologies such as blockages, as seen in the case of sinusitis. Symptoms may include sneezing, itching, nasal congestion, and a runny nose. Non-allergic rhinitis is a diagnosis of rhinitis without any IgE mediation, as documented by allergen skin testing. Hence, the rhinorrhea, sneezing, pruritus, and congestion do not result from allergy or hypersensitivity and continue to persist, whether continuously or sporadically. Non-allergic rhinitis affects 5-10% of the population. Non-allergic rhinitis has 7 basic subclassifications, including infectious rhinitis, non-allergic rhinitis with eosinophilia syndrome (NARES), occupational rhinitis, hormonal rhinitis, drug-induced rhinitis, gustatory rhinitis, and vasomotor rhinitis. Patients may or may not present with the same symptoms seen in allergic rhinitis.

While numerous treatments for rhinitis have been proposed over the years, no single treatment is optimum for all patients or all conditions. Most commonly, hay fever and other forms of rhinitis are treated with antihistamines which block the inflammatory response. While effective, many antihistamines are also undesirable because they can cause drowsiness, or they may have a limited duration of effect, and they can present the patient with an on-going cost associated with continuous purchase of the drugs.

Recently, a longer term therapy for rhinitis which relies on the use of botulinum toxin (BoNT) for blocking mucus production by mucus-producing cells in the nasal membrane has been proposed. Botulinum toxin and other neurotoxins are capable of disabling adrenergic cells, including epithelial or goblet cells which are responsible for the majority of mucus production in the nasal cavity membrane. It has been published in the scientific literature that introduction of botulinum toxin into the nasal passages of canines can reduce mucus secretion by a significant amount.

While the use of botulinum toxin appears to hold promise for long term rhinitis treatment, it faces a number of challenges before it is suitable for wide spread use in humans. In particular, botulinum toxin is a neurotoxin which could have significant negative effects on a patient if accidentally released outside of the targeted nasal passages. Inadvertent distribution of the toxin to muscles of the oropharynx, mouth, tongue, or elsewhere could result in serious complications to the patient. Injection of the toxin helps to overcome some of these issues by directing the toxin to the target area and injection can performed relatively quickly. However, injections also have some challenges that could be overcome, including the fact that injection of the neurotoxin typically requires a local anesthetic to be used, and the fact that many patients are uncomfortable when seeing a needle being inserted into their nostril. Moreover, the use of a needle to inject a toxin deep within the nasal cavity can be very difficult. Topical application of toxins also may have short comings, particularly in terms of the accuracy of delivery of the toxin. For example, the use of botulinum-soaked gauze pads for delivering the toxin to the nasal cavities, as reported in the scientific literature, have limited ability to uniformly and selectively deliver the botulinum to the regions having high concentrations of preferred target cells, such as epithelial or goblet cells in the nasopharynx. Sponges inserted into the nose can be difficult to place, and are hard and uncomfortable when dry, and lack rigidity when wet. Inadvertent compression of a soaked sponge (e.g. against an obstacle during delivery) can result in the drug being squeezed out of the sponge too quickly for adjacent mucosa to absorb the drug, and often in the wrong location. Loading the sponge with a therapeutic agent can also be difficult and time consuming. Aerosol systems have also been proposed for use in delivering a therapeutic agent, but again, precise control of toxin delivery can be a challenge, especially given the dispersement under pressure. Drug eluting balloons have also been suggested for delivery of a therapeutic agent to the sinuses, but require precise positioning.

For these reasons, it would be desirable to provide improved methods and systems for delivering the correct dose of therapeutic agent in a controlled manner to a target treatment site. Such improved methods and systems are preferably used to deliver a toxin, such as botulinum toxin to the nasal membrane of a patient, particularly in a patient suffering from rhinitis or other conditions associated with nasal inflammation and conditions, such as sinus headaches and migraine headaches. Other therapeutic agents including non-toxins may also be delivered. Such systems and methods preferably allow easy delivery without requiring visualization devices such as endoscopes, and preferably do not require anesthesia. The devices preferably have a compact initial shape for insertion and may be easily deployed or activated to expand and fill the desired area of the nasal cavity. The methods and systems should be capable of providing for selective and repeatable delivery of an appropriate dose of the toxins to a defined target areas within the nasal cavities, including particular paranasal sinuses, the nasopharynx, and in some cases substantially the entire nasal cavity. The systems and methods should provide for the safe, accurate and effective delivery of a proper dose of the toxins, and in particular should reduce or eliminate the risk of toxin being delivered to non-targeted tissues outside of the nasal cavity. At least some of these objectives will be met by the inventions described herein below.

2. Description of the Background Art

Patents and publications related to delivery of a toxin to the nasal cavity include U.S. Pat. Nos. 5,766,605 and 6,974,578; and U.S. Patent Publication No. 2005/0281751. Related scientific literature includes Sharri et al. (1995) *Otolaryngol. Head Neck Surg.* 112: 566-571 which further discusses the work disclosed in U.S. Pat. No. 5,766,605. Ünal et al. (2002) *Acta Otolaryngol* 123: 1060-1063 describes the injection of botulinum toxin A into the turbinates of patients suffering from allergic rhinitis. The use of catheters and other devices for the energy-mediated delivery of botulinum light chain is described in commonly owned co-pending U.S. patent application Ser. No. 11/750,967, the entire contents of which are incorporated herein by reference.

BRIEF SUMMARY OF THE INVENTION

Briefly and in general terms, the present invention provides methods and systems for delivery of a therapeutic agent to the nasal cavity. The therapeutic agent may be a toxin or a non-toxin. The present disclosure focuses on preferred embodiments where the invention provides for the delivery of toxin to and across the nasal membrane tissue to treat various conditions and symptoms associated with nasal inflammation, including, rhinorrhea, rhinitis, sinusitis and hay fever. One of skill in the art will appreciate that this is not intended to be limiting and that other therapeutic agents such as non-toxins may also be used.

The region where the toxin is introduced may comprise any portion of the nasal cavity, such as a single paranasal sinus or portion thereof, a main nasal passage, two or more paranasal sinuses, or in some cases may comprise substantially the entire nasal cavity of the patient. A particular target region for the toxin may comprise the nasopharynx which is at the back of the nasal passage. The nasopharynx comprises a cluster of epithelial or goblet cells which are responsible for mucus secretion and which are susceptible to the disabling mechanism of the botulinum toxin and other neurotoxins.

The therapeutic agent to be delivered may be any agent that helps alleviate the symptoms of rhinitis. Preferred therapeutic agents include toxins, and the toxin may comprise any neurotoxin capable of disabling mucus secretion in epithelial or goblet cells and other mucus-producing nasal cells. Preferably, the toxin comprises botulinum toxin, although other toxins such as ricin, exotoxin A, diphtheria toxin, cholera toxin, tetanus toxin, other neurotoxins, and active fragments thereof may also find use.

In addition to the methods described above, the present invention further provides systems for delivering toxins to epithelial or goblet and other target cells as defined above in a nasal membrane.

In a first aspect of the present invention, a system for delivering a therapeutic agent to nasopharyngeal mucosa tissue comprises a shaft having a proximal end and a distal end, a porous pad of compliant material, and a drug reservoir. The porous pad is coupled to the shaft near the distal end, and is configured to expand from a contracted configuration to an expanded configuration. The expanded configuration is adapted to engage and conform to the mucosa tissue in a nasal cavity, and the contracted configuration has a size suitable for introduction into the nasal cavity. The drug reservoir holds a therapeutic agent, and is at least partially covered by the porous pad. The drug reservoir is configured to release a fixed volume of the therapeutic agent into the porous pad within a period of less than about 120 minutes. The drug reservoir has a wall with a plurality of channels that are fluidly coupled with the porous pad.

The elongate central member may comprise an elongate shaft, and the elongate shaft may comprise a central lumen extending therethrough. The elongate shaft may have a lumen that extends between the proximal and distal ends, and the lumen may be fluidly coupled to the drug reservoir. Control of fluid pressure applied to the lumen may control the flow of the therapeutic agent out of the drug reservoir. A sheath may be slidably disposed over the porous pad. The sheath may constrain the porous pad in the contracted configuration, and removal of the sheath from the porous pad may allow expansion thereof into the expanded configuration when the therapeutic agent wets the porous pad. The porous pad may expand from the contracted configuration to the expanded configuration when wetted by the therapeutic agent. The porous pad may exert a force against the mucosa tissue when in the expanded configuration. The system may further comprise a stiffening element extending at least partially from the proximal end to the distal end of the elongate central member. The stiffening member may provide a desired rigidity and stiffness to the elongate central member so that the elongate central member may be delivered to a desired location.

The porous pad may comprises a sponge or a foamed polymer. The porous pad may also comprise a plurality of channels extending radially outward therefrom. The channels may be configured to direct the therapeutic agent toward an external surface of the porous pad. The porous pad may comprise a plurality of fingers extending outward therefrom, or a looped section, or a plurality of protuberances spaced axially apart from one another and separated by a gap therebetween. The porous pad may comprise a plurality of axial elements extending distally of the elongate central member. Each axially extending element may have a portion of the porous pad disposed thereover, and each axially extending element may be in fluid communication with the drug reservoir. The porous pad may comprise a plurality of radial elements extending laterally from the elongate central member. Each radial element may have a portion of the porous pad disposed thereover, and each radial element may be in fluid communication with the drug reservoir. The porous pad may comprise a sheet of porous material wrapped around the elongate central member. The sheet of porous material may be helically wrapped around the elongate central member. The porous pad may comprise a support member disposed therein. The support member may be configured to provide support to the porous pad in the expanded configuration. The porous pad may comprise a plurality of fibers extending radially outward from the central member. The fibers may be configured to be loaded into a syringe in the contracted configuration, and the fibers may expand into engagement with the mucosa tissue when discharged from the syringe and in the expanded configuration. The system may further comprise a hydrophobic layer of material disposed between the drug reservoir and the porous pad. The hydrophobic layer of material may have a plurality of channels disposed therein that are configured to direct the therapeutic agent from the drug reservoir to the porous pad.

The drug reservoir may comprise a plurality of pores that are configured to allow the therapeutic agent to flow from the drug reservoir toward the porous pad. The system may further comprise a plurality of valves fluidly coupled with the plurality of pores. The valves may be configured to control flow through the pores. The system may further comprise a hydrophilic cover surrounding at least a portion of the drug reservoir. The hydrophilic cover may be configured to facilitate transport of the therapeutic agent from the drug reservoir toward an external surface of the porous pad. The drug reservoir may comprise a plurality of loops extending distally from the elongate central member. The loops may have a central reservoir extending therethrough. At least some of the loops may comprise a stiffening member extending therethrough. The stiffening member may be configured to maintain patency of the central reservoirs. The drug reservoir may comprise an expandable member, and expansion of the expandable member may advance the porous pad toward the mucosa tissue. Expansion of the expandable member may also force the therapeutic agent out of the drug reservoir.

In any of the embodiments, the therapeutic agent may comprise a therapeutic agent such as a toxin or other agent including a non-toxin which is configured to inhibit mucus secretions. The toxin may be botulinum toxin.

In another aspect of the present invention, a system for delivering a therapeutic agent to nasopharyngeal mucosa tissue comprises an outer syringe barrel having an elongate flexible sheath extending distally therefrom, and an inner syringe barrel. The inner syringe barrel is slidably disposed in the outer syringe barrel, and the inner syringe barrel has a plunger slidably disposed therein. The inner syringe barrel contains the therapeutic agent and has a tissue penetrating needle extending distally therefrom. Actuation of the plunger discharges the therapeutic agent from the tissue penetrating needle. The tissue penetrating needle is shielded by the outer syringe barrel or the elongate flexible sheath during insertion through the nasal cavity, and distal advancement of the inner syringe barrel relative to the outer syringe barrel slidaby advances the tissue penetrating needle through the elongate flexible sheath to expose a distal tip of the tissue penetrating needle. The system may further comprise an indicator mechanism for indicating quantity of the therapeutic agent discharged from the tissue penetrating needle. The indicator mechanism may provide tactile, auditory, or visual feedback to an operator of the quantity of therapeutic agent discharged.

In yet another aspect of the present invention, a patch for delivering a therapeutic agent to nasopharyngeal mucosa tissue comprises a substrate, a porous reservoir holding the therapeutic agent and coupled to the substrate, and an adhesive layer coupled to the substrate. The adhesive layer is configured to adhere the patch to the mucosa tissue, and the therapeutic agent is released from the porous reservoir into the mucosa tissue when the patch is adhesively engaged therewith. The patch may be flexible and configured to conform to the anatomy of the nasal cavity.

In still another aspect of the present invention, a system for delivering a therapeutic agent to a nasopharyngeal mucosa target comprises a therapeutic agent disposed in a reservoir and a spray device fluidly coupled to the reservoir. The spray device is configured to discharge the therapeutic agent under pressure. The pressure may be high enough so that the therapeutic agent penetrates a mucus blanket disposed over the mucosa tissue. The spray device may be configured to control droplet size of the therapeutic agent discharged therefrom.

In another aspect of the present invention, a system for delivering a therapeutic agent to a nasopharyngeal mucosa target comprises a therapeutic agent disposed in a reservoir, and an applicator having a soft wicking applicator tip. The soft wicking applicator tip is fluidly coupled with the reservoir such that the therapeutic agent is wicked from the reservoir to the wicking applicator tip without applying pressure thereto. The system may further comprise a pressure application member. Actuation of the pressure application member compresses the reservoir and applies a pressure thereto, thereby increasing the flow of therapeutic agent therefrom to the wicking applicator tip. The pressure application member may comprises a plunger.

In still another aspect of the present invention, a method for delivering a therapeutic agent to a nasopharyngeal mucosa tissue comprises inserting a porous pad in a collapsed configuration into a nasal cavity, and with the pad of material inserted in the nasal cavity, wetting the porous pad with a therapeutic agent disposed in a drug reservoir thereby expanding the porous pad into an expanded configuration that engages the mucosa tissue. The method also comprises delivering the therapeutic agent from the porous pad to the mucosa tissue.

The porous pad may be substantially dry during the insertion. A sheath may remain disposed over the porous pad during the insertion. The sheath constrains the porous pad in the collapsed configuration. Wetting the porous pad may comprise opening at least one valve fluidly coupled with the drug reservoir to allow the therapeutic agent to flow therefrom to the porous pad. Pressure may be applied to the drug reservoir thereby pushing the therapeutic agent out of the reservoir. Applying pressure may comprise inflating an expandable member against the drug reservoir. The constraining sheath may be removed from the porous pad, thereby allowing the porous pad to expand into the expanded configuration. The method may further comprise reducing or eliminating the symptoms associated with rhinitis.

In still another aspect of the present invention, a method for delivering a therapeutic agent to nasopharyngeal mucosa tissue comprises advancing an elongate flexible sheath into a nasal cavity with a tissue penetrating needle thereon enclosed within the elongate sheath, and slidably advancing the tissue penetrating needle distally relative to the elongate flexible sheath. The tissue penetrating needle advances through the elongate flexible sheath so that a tissue penetrating tip of the tissue penetrating needle is exposed. The method also comprises piercing the nasopharyngeal mucosa tissue with the piercing needle, and delivering a therapeutic agent from the tissue penetrating needle to the nasopharyngeal mucosa tissue.

The elongate flexible sheath may be coupled to and extend distally from an outer syringe barrel. Advancing the elongate flexible sheath may comprise moving the outer syringe barrel toward the nasal cavity. The tissue penetrating needle may be coupled to and extend distally from an inner syringe barrel. Slidably advancing the tissue penetrating needle may comprise distally moving the inner syringe barrel relative to outer syringe barrel.

Piercing may comprise distally advancing the inner syringe barrel relative to the outer syringe barrel such that the inner syringe barrel slides through the outer syringe barrel. Delivering the therapeutic agent may comprise discharging the therapeutic agent from an inner syringe barrel. Delivering the therapeutic agent may comprise controlling the quantity of the therapeutic agent delivered by monitoring a visual, tactile, or auditory indicator mechanism. The method may further comprise reducing or eliminating the symptoms associated with rhinitis.

In another aspect of the present invention, a method for delivering a therapeutic agent to nasopharyngeal mucosa tissue comprises inserting a patch carrying a therapeutic agent into a nasal cavity, and attaching the patch to the nasopharyngeal mucosa tissue. The method also comprises delivering the therapeutic agent from the patch to the nasopharyngeal mucosa tissue.

The patch may be flexible and may be in a collapsed configuration during insertion. Adhering the patch may comprise expanding the patch from the collapsed configuration into an expanded configuration so that the patch may conform to the anatomy of the nasal cavity. Attaching the patch may comprise adhesively bonding the patch to the nasopharyngeal mucosa tissue. The patch may comprise a porous reservoir holding the therapeutic agent, and delivering the therapeutic agent may comprise discharging the therapeutic agent from the porous reservoir to an outer surface of the patch. The method may comprise reducing or eliminating symptoms associated with rhinitis.

In another aspect of the present invention, a method for delivering a therapeutic agent to nasopharyngeal mucosa tissue comprises providing a spray device having a reservoir that holds a therapeutic agent, pressurizing the reservoir, and spraying the therapeutic agent onto the nasopharyngeal mucosa tissue. Pressurizing may comprise pressurizing the reservoir to a pressure sufficient enough such that when sprayed, the therapeutic agent penetrates a mucus blanket disposed over the mucosa tissue. The method may further comprise controlling droplet size of the sprayed therapeutic agent. The method may further comprise reducing or eliminating symptoms associated with rhinitis.

In yet another aspect of the present invention, a method for delivering a therapeutic agent to nasopharyngeal mucosa tissue comprises providing an applicator having a reservoir that holds a therapeutic agent, and advancing a soft wicking tip disposed on a distal portion of the applicator into a nasal cavity. The method also includes painting the nasopharyngeal mucosa tissue with the soft wicking tip wherein the therapeutic agent is wicked from the reservoir to the soft wicking tip thereby applying a layer of the therapeutic agent to the nasopharyngeal mucosa tissue. The method may further comprise applying pressure to the reservoir thereby increasing flow of the therapeutic agent from the reservoir to the soft wicking tip and onto the nasopharyngeal mucosa tissue. The method may reduce or eliminate symptoms associated with rhinitis.

In another aspect of the present invention, a system for delivering a therapeutic agent to nasopharyngeal mucosa tissue comprises an elongate shaft having a proximal end and a distal end, an inner expandable member and an outer expandable member. The inner expandable member is disposed near the distal end and has a contracted configuration sized for introduction into the nasal cavity and an expanded volume configuration adapted to engage and conform to the mucosa tissue in a nasal cavity. The outer expandable member is disposed over the inner expandable member and has a contracted configuration sized for introduction into the nasal cavity and an expanded volume configuration adapted to fill the nasal cavity. The system also has a therapeutic agent carried by the outer expandable member and that is adapted to inhibit mucus secretions.

The inner expandable member may comprise a balloon. The outer expandable member may also comprise a balloon or a sponge. The inner or outer expandable member may comprise a plurality of pores that are configured to allow the therapeutic agent to pass therethrough. The therapeutic agent may comprise a toxin such as botulinum toxin.

In yet another aspect of the present invention, a method for delivering a therapeutic agent to nasopharyngeal mucosa tissue comprises providing a delivery system having a first expandable member and a second expandable member disposed thereover. The first and second expandable members each have a collapsed configuration and an expanded configuration. The first expandable member is inserted in the collapsed configuration into a nasal cavity and the expanded from the collapsed configuration to the expanded configuration thereby filling up the nasal cavity. The second expandable member is expanded from the collapsed configuration to the expanded configuration so as to engage the mucosa tissue in the nasal cavity. The therapeutic agent is then delivered from the expandable member to the mucosa tissue.

Expanding the first or second expandable member may comprise inflating a balloon. Expanding the second expandable member may comprise expanding a sponge. The expanded configuration of the first expandable member may have a larger volume than the expanded configuration of the second expandable member. Delivering the therapeutic agent may comprise delivering a toxin such as botulinum toxin.

These and other embodiments are described in further detail in the following description related to the appended drawing figures.

DETAILED DESCRIPTION OF THE INVENTION

The present invention is preferably directed to methods and systems for delivering one or more therapeutic agents including toxins or non-toxins to target cells within a patient's nasal cavity. The toxins may be intact toxins, such as botulinum toxin, ricin, exotoxin A, diphtheria toxin, cholera toxin, tetanus toxin, other neurotoxins, and active fragments thereof. Each of these toxins comprises a heavy chain responsible for cell binding and a light chain having enzyme activity responsible for cell toxicity.

Botulinum toxin blocks acetylcholine release from cells, such as the epithelial or goblet cells in the nasal membranes responsible for mucus hypersecretion, and can thus be effective in accordance with the principles of the present invention. The use of energy to permeablize or porate the cell membranes of the epithelial or goblet cells or other mucus-secreting cells of the nasal lining, may facilitate botulinum and other toxins to be preferentially delivered to the targeted epithelial or goblet and other mucus-producing cells. Additionally, energy-mediation allows use of the active or light chains of these toxins (having the heavy chains removed or inactivated) for treatments. Normally, the light chains when separated from the cell-binding heavy chains of botulinum and the other toxins are incapable of entering the cells and thus will be free from significant cell toxicity. By using energy-mediated protocols the toxin light chains may be locally and specifically introduced into the target cells located within defined regions of the nasal membrane. Thus, even if the toxin fragments are accidentally dispersed beyond the desired target regions, the fragments will not generally enter cells without the additional application of cell permeablizing or porating energy. For that reason, toxin delivery methods are particularly safe when performed with toxin fragments, such as the light chain of botulinum and other toxins.

While the remaining portion of this disclosure will be presented with specific reference to the botulinum toxin, one of skill in the art will appreciate that other toxins may also be used, including the active fragment of the toxin in combination with energy-mediated delivery protocols such as those disclosed in U.S. Patent Applications previously incorporated by reference above.

Figure 1:
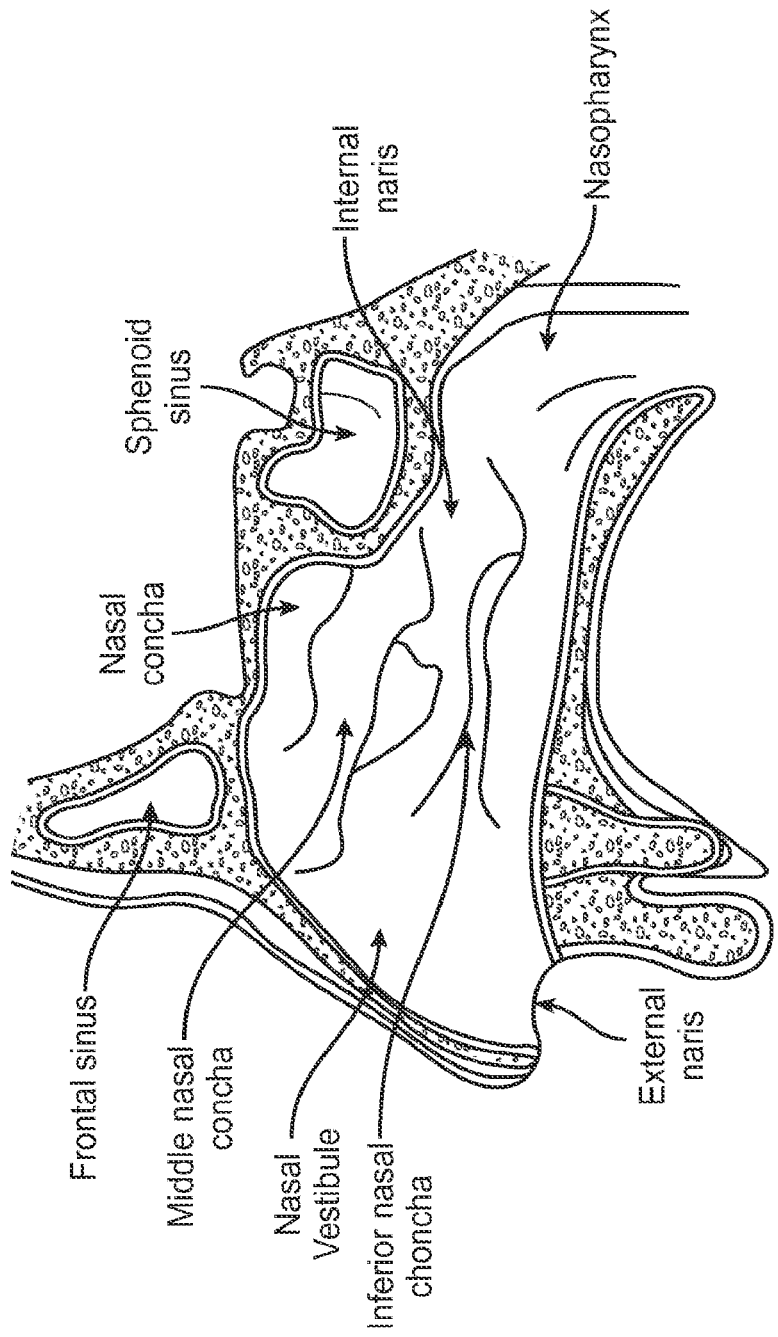
FIG. 1 illustrates basic anatomy of the nasal cavity.

FIG. 1 illustrates the basic anatomy of the nasal cavity. The entrance to the nasal cavity is via the external naris. The anterior-most portion of the nasal cavity is referred to as the nasal vestibule and is enclosed by cartilage and lined by epithelium. Small hairs in the vestibule help filter dust and other contaminants in the air that is breathed in. Long, narrow, and curled bone shelves line a portion of the nasal cavity. These bones are referred to as nasal concha or turbinates. An upper or superior turbinate, a middle turbinate, and an inferior turbinate divide the nasal airway into four channel-like air passages which direct inhaled air to flow in a steady, regular pattern around the largest possible surface of cilia and climate controlling tissue. Various sinus cavities are also disposed within the bones of the face and skull adjacent the nasal cavity. These sinuses, such as the frontal sinus and the sphenoid sinus are mucosa lined airspaces that produce mucus. The nasal cavity communicates with the throat via the nasopharynx.

Foam Covered Reservoir Embodiments

Figure 2A:
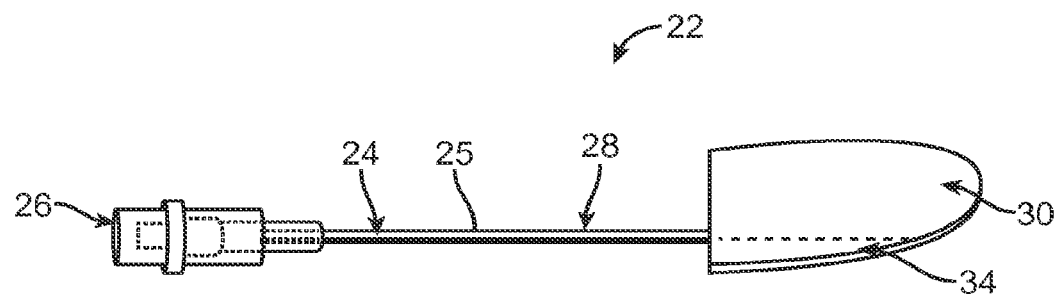
FIGS. 2A-2B illustrate an exemplary delivery device having a covered porous reservoir.
Figure 2B:
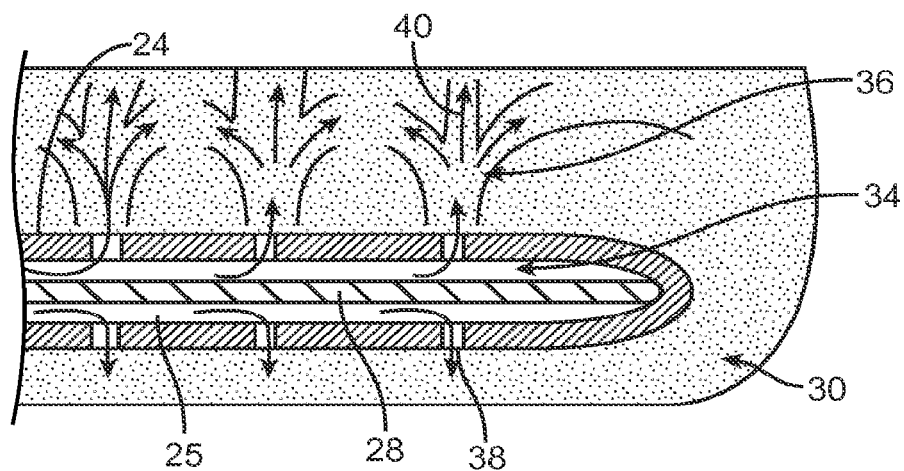
Figure 3A:
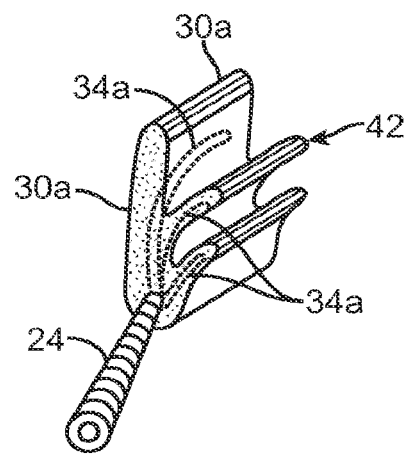
FIGS. 3A-3E illustrate other exemplary delivery devices of a covered porous reservoir with cover configurations.
Figure 3B:
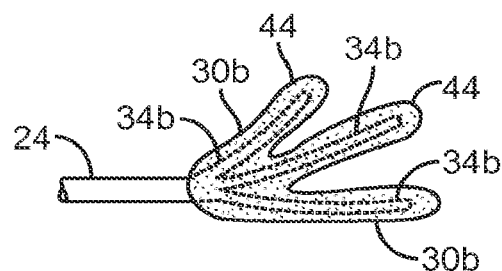
Figure 3C:
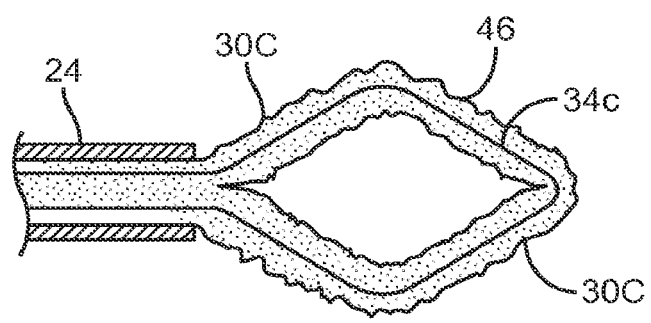
Figure 3D:
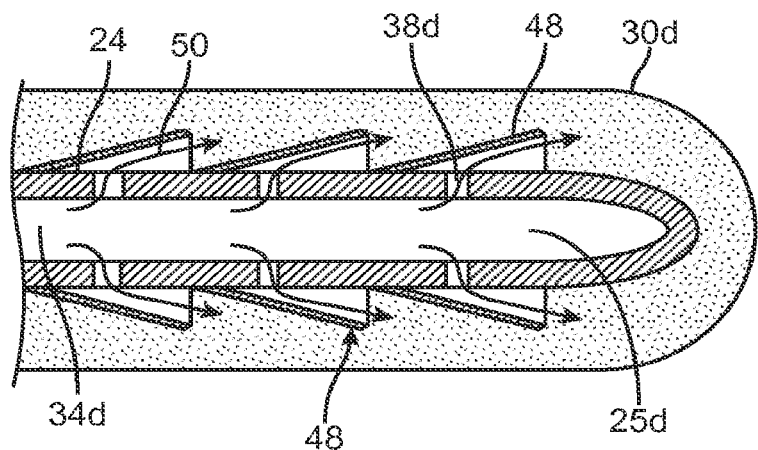
Figure 3E:
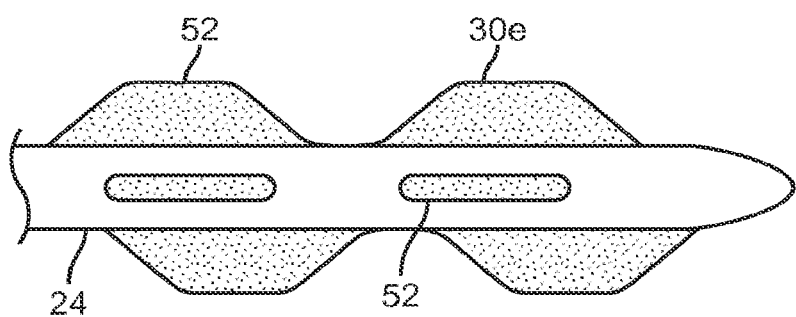
Figure 4:
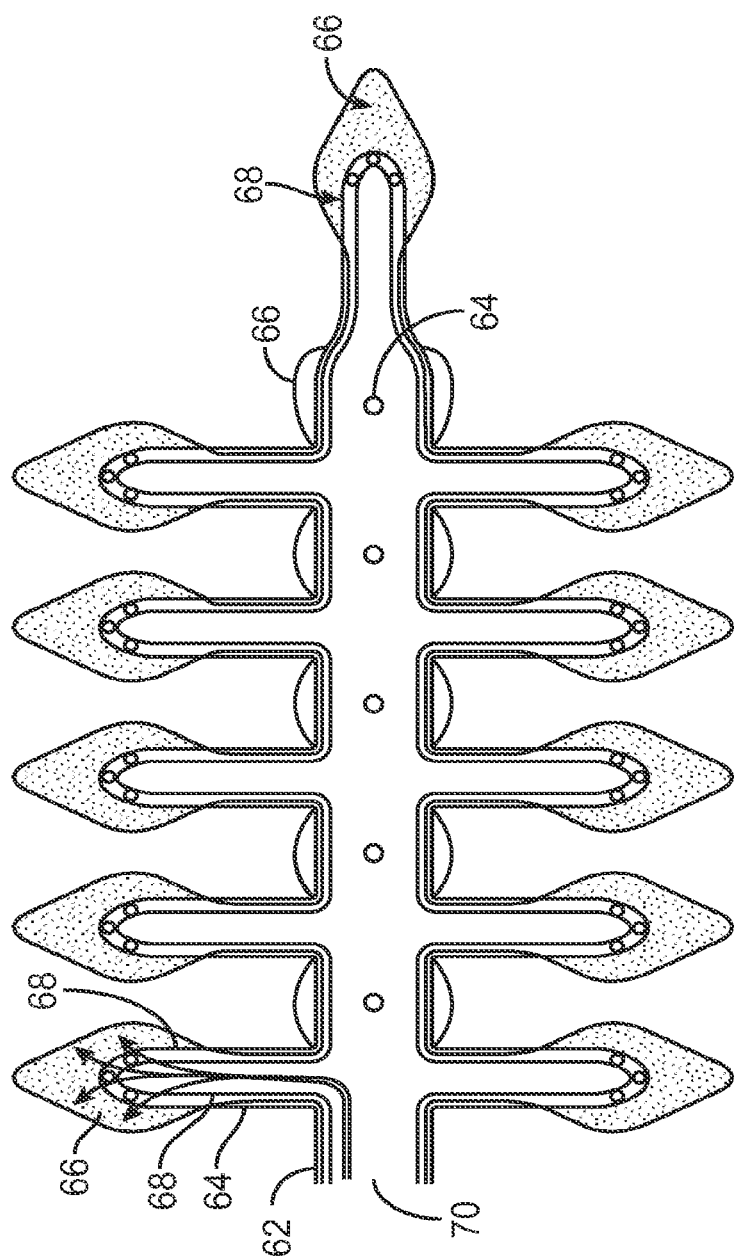
FIG. 4 illustrates still another exemplary embodiment of a delivery device with a porous reservoir and an alternative cover configuration.

FIGS. 2A-2B illustrate an exemplary embodiment of a delivery device having a porous reservoir with a soft covered tip. The delivery device 22 includes an elongate catheter shaft 24 having a lumen 25 therethrough. The proximal end of the delivery device 22 includes a standard connector 26 such as a Luer connector for fluidly coupling the delivery device 22 with a source of the toxin, or other therapeutic agent to be delivered therefrom. In preferred embodiments, the connector 26 also has a one-way valve to prevent the therapeutic agent, here a toxin such as botulinum toxin from leaking out of the proximal end of the shaft 24. The distal portion of the delivery device 22 includes a soft covered portion, here a resilient foam contact element 30 that is disposed around the shaft 24. A wire support 28 extends through the lumen 25 of elongate shaft 24 and provides stiffness to the shaft to facilitate advancement into the nasal cavity, and prevent kinking or unwanted bending. Other support members including wires, plastic members, nitinol components, sutures, foam elements, etc. may also be coupled to various portion of the delivery system in order to help provide support.

FIG. 2B is a cross-section of the resilient foam contact element 30. The elongate shaft 24 extends under the foam contact element 30, and support wire 28 preferably extends through lumen 25 of the elongate shaft 24 under foam contact element 30. One or more pores 38 extend laterally through the sidewall of shaft 24 so that they are in fluid communication with lumen 25 which serves as a reservoir 34 for the toxin or therapeutic agent to be delivered. The reservoir 34 may also be a pressure filled bladder. The reservoir 34 may extend only under the foam contact element 30, or it may extend proximally beyond the foam contact element 30 into shaft 24. Foam contact element 30 may be a hydrophilic material to help hold and distribute the therapeutic agent. The foam contact element 32 also may include channels 36, perforations, or slits which help direct the therapeutic agent to flow 40 from the lumen 25 which acts as reservoir 34, through the pores 38 in the shaft sidewall, through the foam contact element 30 to a surface of the foam contact element for delivery to the target tissue which in this embodiment is preferably nasopharyngeal mucosa tissue. Thus, in this embodiment, a syringe or other device may be coupled to the connector 26 and the lumen may be filled with a therapeutic agent. Thus the lumen 25 acts as a reservoir for the therapeutic agent. The therapeutic agent will be absorbed by the foam contact element for delivery to the tissue. Additional actuation of the syringe may be used to pressurize the therapeutic agent within the reservoir to help it flow outward into the foam contact element. Thus, the foam contact element acts as an absorbent and porous pad. Additionally, the foam contact element, which may be made from any number of polymeric foam materials or woven or nonwoven materials including fabrics or synthetics, is preferably resilient so that it may have a collapsed low profile configuration suitable for delivery through the confined space of the nostrils and nasal cavity, and also have an expanded larger profile for maximum tissue contact. The foam contact element may be constrained in the low profile collapsed configuration with a sheath, cannula, or other constraining element (not illustrated), and it may expand once the sheath or constraining element is removed. In preferred embodiments, the foam contact element in the collapsed configuration has a cross-section less than or equal to a 6 mm diameter cylindrical shaft. Additionally, wetting of the foam contact element with the therapeutic agent may further facilitate expansion thereof.

The embodiment of FIGS. 2A-2B has a cylindrical shaped body with a tapered nosecone. Any number of other geometries for the foam contact element are also possible. For example, FIGS. 3A-3E illustrate other exemplary embodiments of foam contact elements that can be used as a porous pad to deliver a therapeutic agent to the target tissue. Other aspects of the delivery device may generally take the same form as device 22 previously described above.

FIG. 3A illustrates a delivery device having an elongate shaft 24 with a foam contact element **30*a* adjacent a distal portion of the elongate shaft 24. The foam contact element 30*a* has a plurality of wings 42 extending therefrom. The wings 42 may be sized and shaped in order to accommodate various sizes and anatomies in the nasal cavity. The wings 42 may be fabricated from any of the materials previously discussed with reference to device 22 in FIGS. 2A-2B. A porous reservoir 34*a* similar to reservoir 34 in FIG. 2B may extend under each wing 42 in order to ensure even distribution of therapeutic agent to each wing 42. The wings 42** may also be collapsed for delivery, and expanded into engagement with target tissue.

FIG. 3B illustrates another exemplary embodiment of a delivery device that generally takes the same form as the device in FIG. 3A, with the major difference being that the foam contact element **30*b* on a distal portion of the elongate shaft 24 has a plurality of fingers 34*b* which extend distally from elongate shaft 24. In this embodiment, three fingers 34*b* form a pattern similar to a bird footprint. One of skill in the art will appreciate that the length, thickness, and number of fingers may be adjusted to fit the nasal cavity being treated. A porous reservoir 34*b* similar to the reservoirs previously described may be disposed in each finger 34*b* of the foam contact element 30*b***.

FIG. 3C illustrates yet another exemplary embodiment of a delivery device that generally take the same form as previous delivery devices discussed above, with the major difference being that the foam contact element **30*c* includes a looped element 46 extending distally from the elongate shaft 24. A porous reservoir 34*c* similar to those described above extends through the loop 46 so that the therapeutic agent is evenly distributed along the loop. The loop 46 may be retracted into the shaft 24 for delivery, or a constraining sheath (not shown) may be passed over the loop to compress it into the collapsed configuration for delivery into the nasal cavity. Upon reaching a desired target treatment site, the sheath may be retracted, or the loop 46 may be advanced from the shaft 24 so that the loop is unconstrained and expands into its fully expanded configuration to engage the tissue. The loop 46 may be a foam, a foam-wrapped structural element, or any of the other materials previously described above with reference to device 22 in FIGS. 2A-2B**.

FIG. 3D illustrates an exemplary embodiment of a delivery device having valves. Other features of the device generally take the same form as the previous delivery devices described above. Elongate shaft 24 extends under the foam contact element **30*d*. A lumen 25*d* extends through shaft 24, and a plurality of ports 38*d* pass through a sidewall of the shaft 24 such that they are fluidly coupled to lumen 25*d* which when filled with a therapeutic agent such as botulinum toxin serves as a drug reservoir 34*d*. Valves 48 cover each port 38*d* and they are resiliently biased to close and rest against ports 38*d* thereby fluidly closing the ports 38*d*. However, when the reservoir is pressurized with a therapeutic agent, the valves 48 open up allowing the therapeutic agent to flow 50 and be discharged from the reservoir into the foam contact element 30*d***.

In still another exemplary embodiment, the foam contact element **30*e* may comprise a plurality of axially spaced apart bumps 52 which form fins along the elongate shaft 24. In this embodiment, four rows of fins are evenly spaced ninety degrees apart around the circumference of shaft 24. Each row is axially staggered relative to an adjacent row. The number of fins, number of rows, axial offset, circumferential offset, as well as other aspects of the fin arrangement may be varied according to the anatomy or other relative design criteria. Other aspects of the delivery device in FIG. 3E** generally take the same form as those previously described above.

FIG. 4 illustrates another exemplary embodiment of a delivery device used to deliver a therapeutic agent such as a toxin like botulinum toxin to tissue. The delivery device includes an elongate central shaft 62 and having a lumen 70 extending therethrough. A plurality of fingers 64 extend radially outward from shaft 62. Each finger has a central channel that is fluidly coupled with lumen 70, and each finger 64 has one or more ports 68 through a sidewall that allow fluid to egress from the finger into a foam contact element 66. Thus, a therapeutic agent such as botulinum toxin may be introduced into lumen 70 and the lumen acts as a drug reservoir. The drug may then be discharged from lumen 70, into the fingers and out ports 68 until the therapeutic agent wets foam contact element 66. The fingers 64 preferably extend perpendicularly from shaft 62, however, the fingers may extend at any desired angle. In this embodiment, four rows of fingers are distributed around the circumference of shaft 62, each row spaced ninety degrees apart from one another. Additionally, adjacent rows are axially offset from one another, or staggered. The distal end of shaft 62 may also include a finger with ports 68 and foam contact element 66. Thus, the delivery device in FIG. 4 may appear to be similar to the pattern used for bottle brushes. One of skill in the art will appreciate that the number of rows of fingers, axial spacing between adjacent rows, as well as circumferential spacing of rows of fingers, and other aspects of geometry may be modified depending on usage.

FIGS. 5A-5F illustrate how a single sheet of laminated material may be used to form a drug reservoir and foam contact element of a delivery device similar to those described above. In FIG. 5A, a single sheet of material, comprising a laminate of a support structure 82 such as a wire frame or other substrate material laminated to an inner liner **88*a* having a plurality of ports 88 extending through the liner wall, and a foam material or other porous pad 86 laminated to the liner. The laminated sheet of material may then be formed into various configurations to form the drug reservoir portion and tissue engaging portion of a drug delivery device. For example, in FIG. 5A, the laminated sheet of material may be folded over itself with the edges sealed to form a lumen 84 which holds the therapeutic agent and thus functions as a drug reservoir 89. The proximal end of the folded laminated sheet may then be coupled to an elongated shaft similar to those discussed above. Thus, in FIG. 5A, the drug is introduced via a lumen in an elongated shaft into lumen 84 where it is stored in reservoir 89. The device may be advanced through a nostril into the nasal cavity, and the drug flows 90 through ports 88 into foam contact element 86. The drug wets the foam contact element 86**, and then the drug is delivered to the nasopharyngeal mucosa tissue.

Figure 5A:
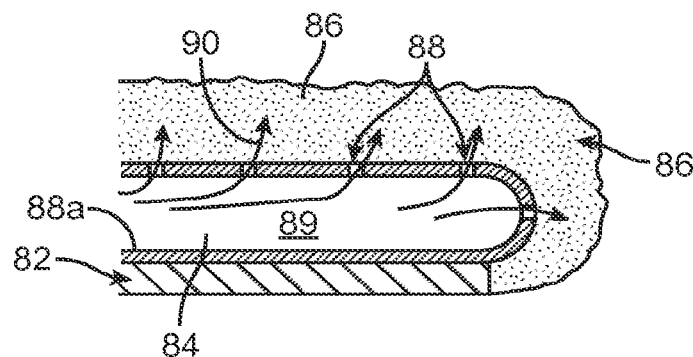
FIGS. 5A-5F illustrate use of a single sheet of material to form a portion of a drug delivery device.
Figure 5B:
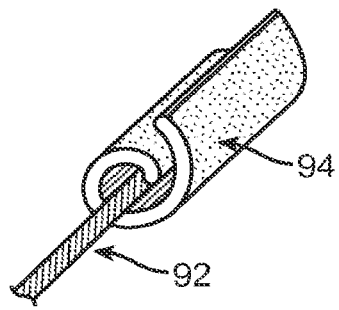
Figure 5C:
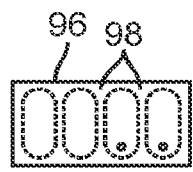
Figure 5D:
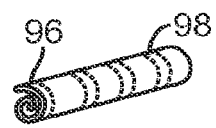
Figure 5E:
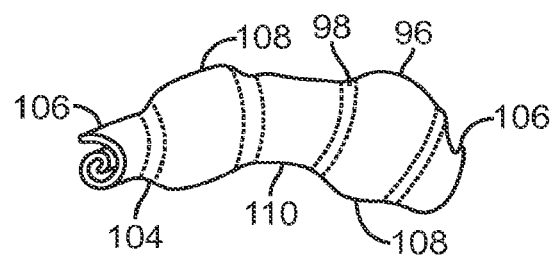

FIG. 5B illustrates another exemplary embodiment where the laminated sheet 94 similar to that in FIG. 5A is rolled up on itself like a cinnamon roll and coupled to an elongate shaft 92 to form the drug delivery device. FIG. 5C illustrates the laminated sheet 96 in a flat unrolled configuration. It may include structural support features 98 such as ribs, support wires, or other structural elements that help it to form cylindrical rolls such as in FIG. 5D. FIG. 5E illustrates another possible configuration that may be formed by rolling the laminated sheet 96. It includes lower profile proximal and distal ends 106 which may be attached to an elongate shaft (not illustrated), as well as proximal and distal enlarged profile collars and a smaller middle profile region 110. Thus different portions of the length of the device can expand to different diameters based on the surrounding anatomy. This configuration may be useful for accommodating and treating various anatomical areas of the nasal cavity.

Figure 5F:
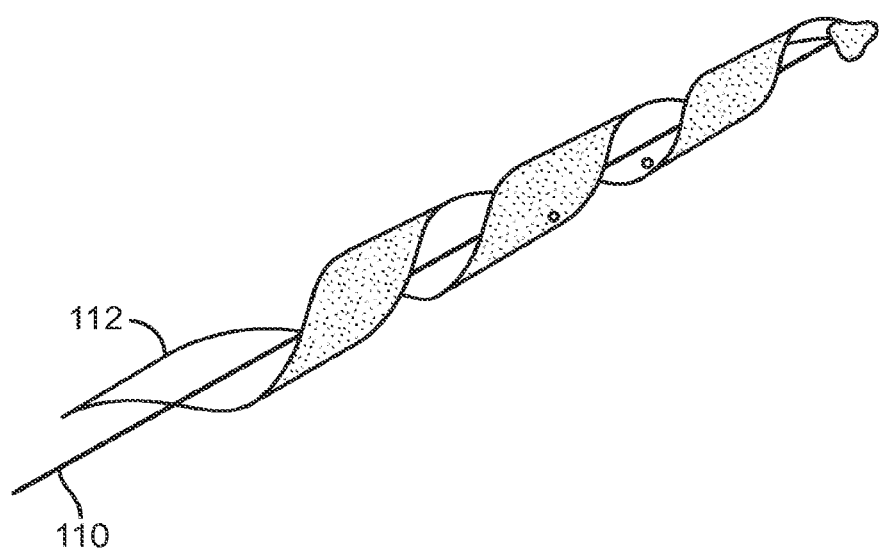

FIG. 5F illustrates still another exemplary embodiment of how the laminated sheet may be formed into a drug delivery device. An elongate shaft or push wire 110 may be used to wrap the laminated sheet 112 around the shaft to form a helix or corkscrew pattern. Rotation and/or linear advancement of the push wire relative to the laminated sheet 112 may expand or contract the helix, thereby increasing or decreasing its profile. This may be advantageous since it allows the device to be delivered into the nasal cavity in a low profile configuration, and then it may be easily expanded to engage the nasopharyngeal mucosa tissue.

Figure 6:
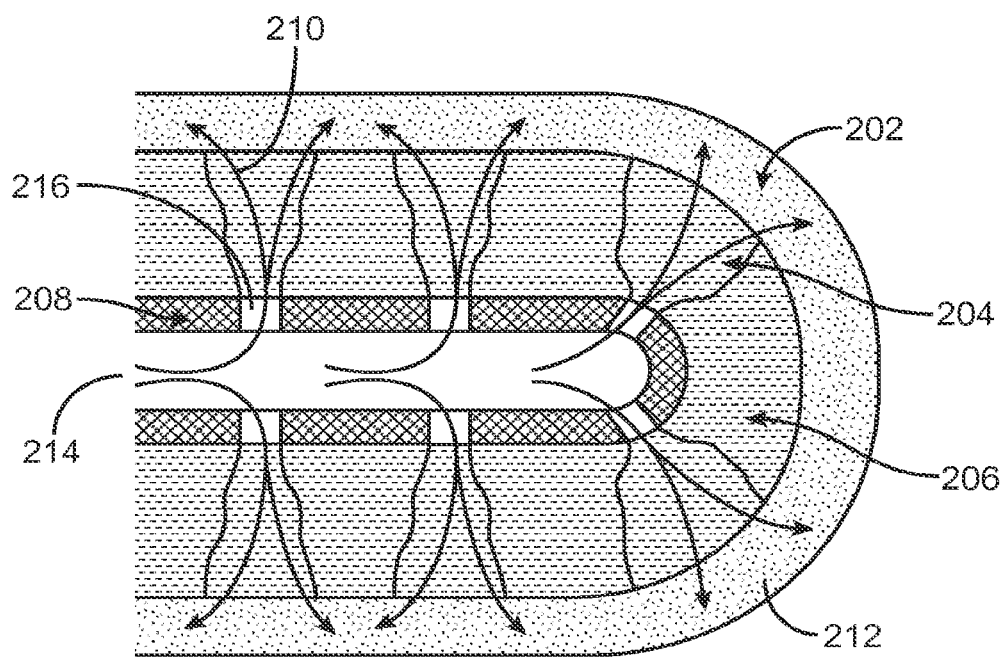
FIG. 6 illustrates an alternative embodiment of a foam contact element.

FIG. 6 illustrates an alternative embodiment of a foam contact element or porous pad material that may be used with any of the foam contact element embodiments described herein. The foam contact element 212 may be coupled to an elongate shaft as previously described above, or it may be coupled to other delivery instruments, or used alone. The foam contact element 212 includes an outer foam layer 202 that surrounds the porous reservoir 208 having a central lumen 214 for holding a therapeutic agent, and pores 216 that allow the therapeutic agent to be released therefrom. A layer of hydrophobic foam 206 is disposed between the outer foam layer 202 and the porous reservoir 208. Channels 204 are disposed in the hydrophobic foam layer 206 and they help direct the therapeutic agent to the outer foam layer 202. This configuration provides a large outer surface area for contact with tissue for delivering the therapeutic agent, while minimizing the volume of therapeutic agent that is absorbed into the foam due to the hydrophobic layer.

Figure 7A:
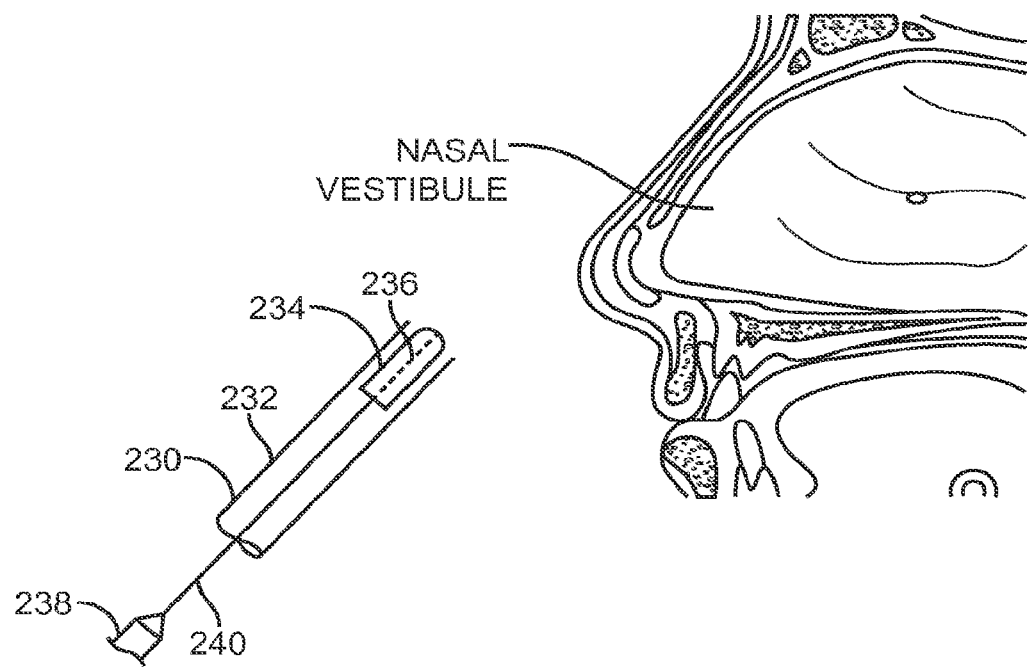
FIGS. 7A-7B illustrate an exemplary method of delivering a therapeutic agent to a nasal cavity.
Figure 7B:
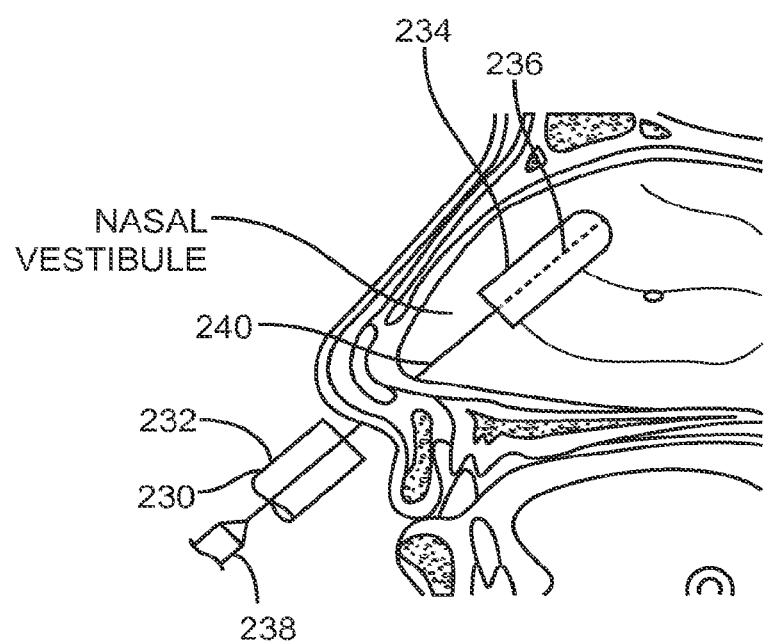

FIGS. 7A-7B illustrate an exemplary method of delivering a therapeutic agent to the nasal cavity with a foam contact element. The delivery device 230 includes an elongate shaft 240 having a foam contact element 234 similar to those described above, adjacent a distal portion of the elongate shaft 240. Disposed under the foam contact element 240 lies a porous reservoir 236 similar to those previously described above. A connector 238 coupled to the proximal end of the elongate shaft 240 allows a syringe or other device to be fluidly coupled to the elongate shaft and the porous reservoir. An optional sheath 232 may be slidably disposed over the foam contact element 234 to constrain the foam contact element into a collapsed configuration that facilitates insertion into the nasal cavity via a nostril. In FIG. 7B, the delivery device 230 has been advanced into the nasal cavity via a nostril, and sheath 232 has been proximally retracted, thereby allowing the foam contact element to expand into engagement with nasopharyngeal mucosa tissue. The shape of the foam contact element may be varied as discussed above in order to engage specific regions of the nasal cavity. Possible targets include any of the turbinates as well as the nasal septum, uncinate process, inferior, superior, and lateral extents of the nasopharynx. The therapeutic agent, such as botulinum toxin may then be released from the reservoir 236 into the foam contact element 234 and delivered to the tissue. The reservoir may be pre-filled, or a syringe or other device may also be coupled to connector 238 to deliver the therapeutic agent to the reservoir and/or to pressurize the reservoir to facilitate its delivery. Wetting of the foam contact element may further result in expansion of the foam contact element so that it contacts an even larger surface area. The size of the foam contact element may be selected depending on the size of the nasal cavity, or the size of the target area to treat. In alternative embodiments, multiple delivery devices may be used to treat a larger area.

The delivery device in FIGS. 7A-7B may be used to treat symptoms associated with rhinitis. A toxin may be used such as botulinum toxin that reduces or inhibits mucus production. In an exemplary embodiment, 50 U of botulinum toxin A may be hydrated with saline per manufacturer's recommendations to a concentration of 25 U/ml. Each side of the nose may then be treated with 1 ml of the therapeutic agent, resulting in delivery of 25 U to the tissue. Dosage may vary, and can be as little as 10 U or as large as 200 U. Concentration can vary and may be as great as 100 U/ml. In preferred embodiments the delivery device is configured to deliver the full dosage of the therapeutic agent to the tissue within 30 minutes, however depending on concentration of the substance, it may be preferable to deliver more slowly (e.g. over 60 minutes), or more rapidly (e.g. in one to two minutes). Delivery may also occur over a time period somewhere in between these slower and faster time periods. Also, in this as well as other embodiments, the therapeutic agent may be chemically modified to help with absorption through the skin, such as by forming salts of the drug having increased solubility, or by forming esters of the drug that help increase permeability of the mucus membranes. The use of surfactants may also help modify mucosa permeability. Drugs may also be modified to have increased hydrogen bonding thereby allowing increased mucoadhesiveness to prevent the therapeutic agent from migrating to undesirable areas. Other modifications to the therapeutic agent include the use of bioadhesive polymers such as polyacrylic acid to form a gel-like layer that enhances contact between the drug and the tissue, resulting in increased residence time of the agent. Microspheres, nanoparticles, and liposomes may also be used to help with mucoadhesiveness.

Figure 8A:
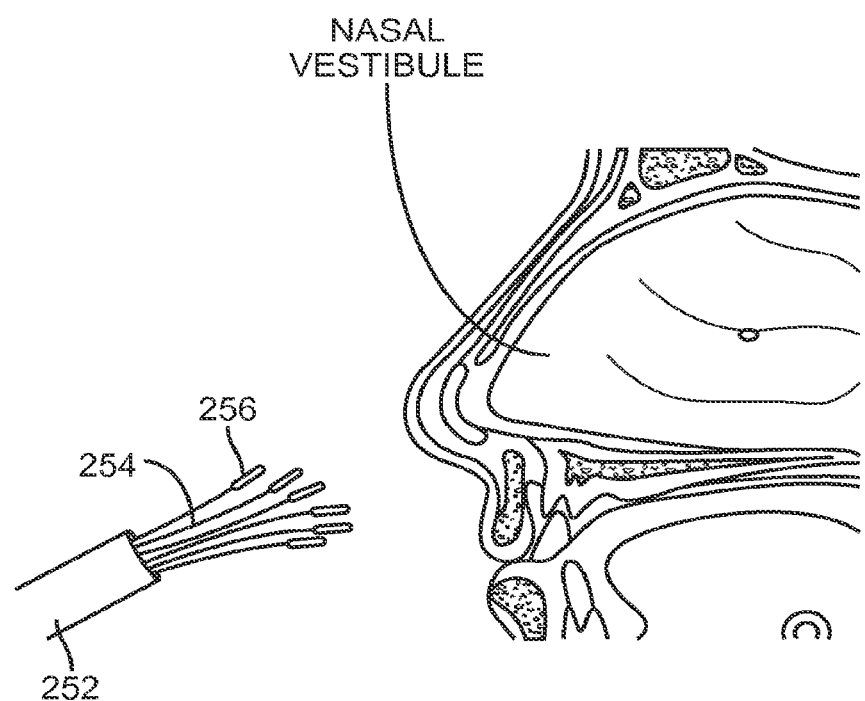
FIGS. 8A-8B illustrate another exemplary method of delivering a therapeutic agent to a nasal cavity.
Figure 8B:
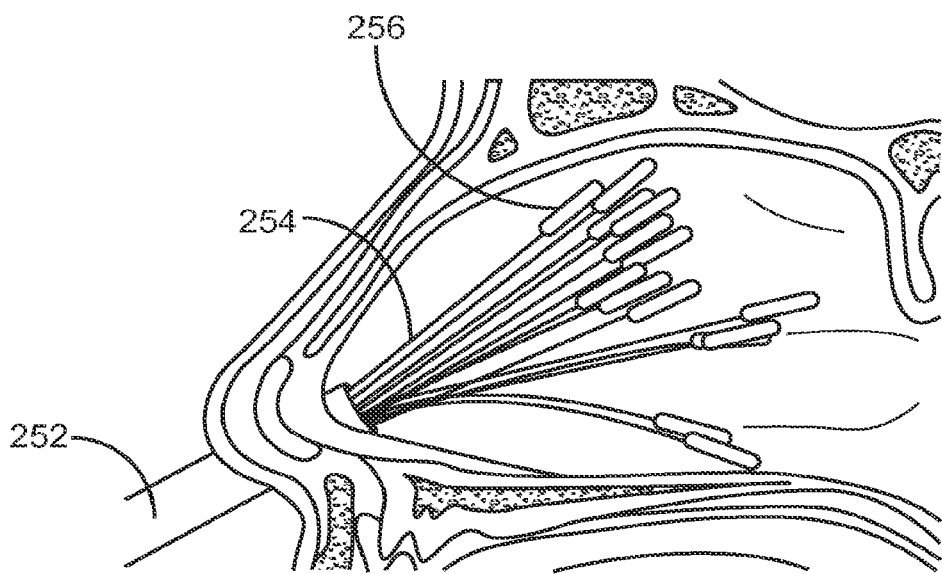

FIGS. 8A-8B illustrate another exemplary embodiment of delivering a therapeutic agent to the nasal cavity. The delivery device includes a plurality of flexible shafts 254, each having a foam contact element 256 disposed on a distal portion of the flexible shaft 254. A porous reservoir (not illustrated) similar to those previously described is disposed under the foam contact element. An outer sheath 252 is slidably disposed over the plurality of shafts 254, and the sheath 252 may partially cover the shafts 254 or entirely cover the shafts 254 and foam contact elements 256. Thus sheath 252 helps constrain the shafts 254 into a lower profile for ease of insertion into the nasal cavity. In FIG. 8B, the delivery device has been advanced into the nasal cavity via a nostril. The sheath 252 has been retracted relative to the plurality of flexible shafts 254 allowing the foam contact elements 256 to fan out and contact a larger area of tissue. The therapeutic agent may then be discharged from the porous reservoir into to the foam and to the tissue, as described previously. Use of multiple flexible shafts and contact elements allow the device to reach smaller, harder to reach areas within the nasal cavity, as well as to more easily navigate around obstructions or through narrow gaps. A delivery device may be used in each side of the nose, and multiple delivery devices may be used on a single side.

Figure 9A:
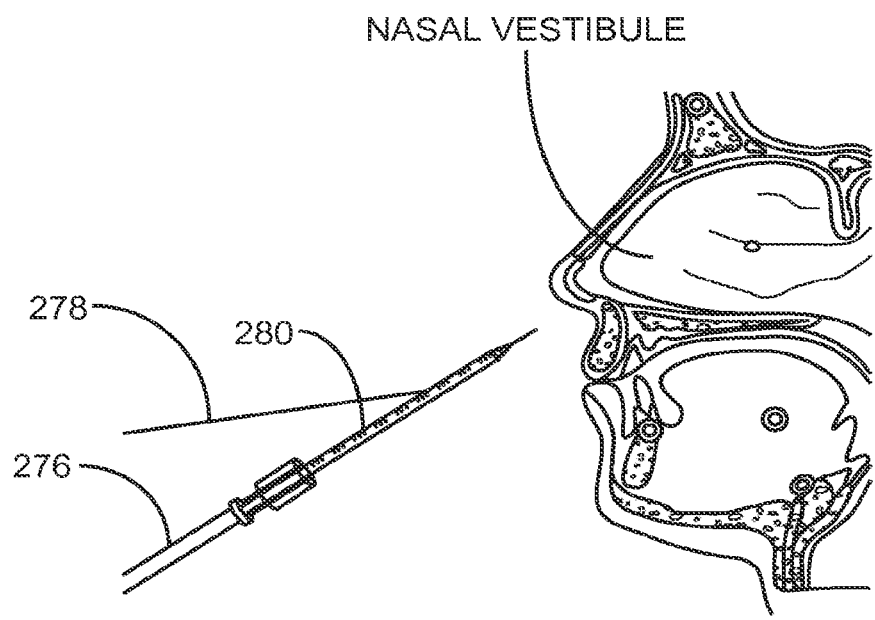
FIGS. 9A-9B illustrate still another exemplary method of delivering a therapeutic agent to a nasal cavity.
Figure 9B:
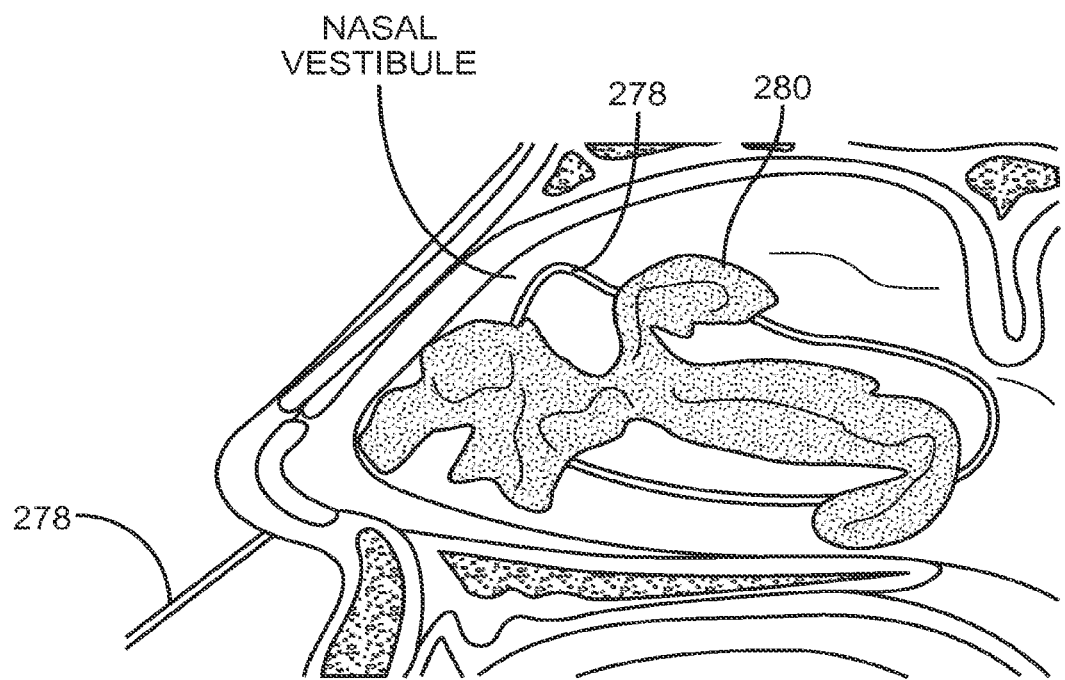

FIGS. 9A-9B illustrate still another exemplary embodiment of a method for delivering a therapeutic agent to the nasal cavity. A porous reservoir (not illustrated, but similar to that previously described above) may include a small diameter flexible tube covered with foam or another expandable and absorbable pad of material. Pores in the reservoir allow a therapeutic agent to be released therefrom into the foam cover for delivery to the tissue. The foam covered flexible tube 280 may be loaded into a syringe 276 for advancement through a nostril into the nasal cavity as seen in FIG. 9A. Once the syringe is advanced into the nasal cavity, the syringe plunger may be actuated and the foam covered flexible tube 280 is pushed out of the syringe into the nasal cavity as seen in FIG. 9B. Once unconstrained by the syringe, the foam expands to fill the nasal cavity. A string 278 is coupled to the foam covered flexible tube, and a free end of the string 278 remains outside of the nostril. The free end of the string may be pulled in order to remove the foam covered flexible tube. Multiple foam covered tubes may be inserted into the nasal cavity in order to deliver the therapeutic agent to a larger surface area.

Additional Delivery Device Embodiments

In addition to the embodiments previously described, other exemplary embodiments are possible. For example, the drug delivery device may include looped elements for delivering the therapeutic agent, a pressurized drug reservoir, porous balloons, retractable needles, patches, and paint brush-like embodiments.

Figure 10:
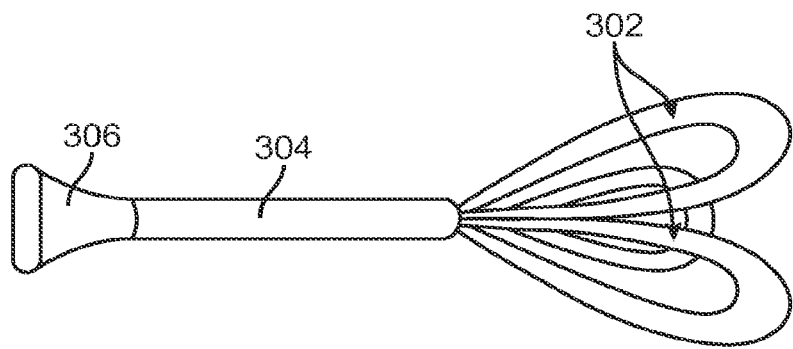
FIG. 10 illustrates an exemplary embodiment of a device for delivering a therapeutic agent to a nasal cavity.
Figure 11:
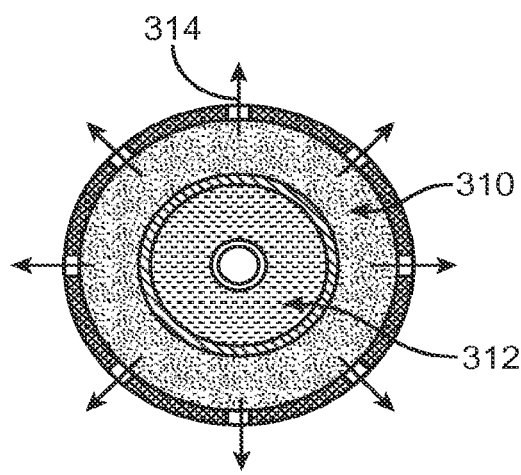
FIG. 11 illustrates an exemplary embodiment of a pressurized drug reservoir.

FIG. 10 illustrates a delivery device having a plurality of looped distal elements 302 coupled to shaft 304. A connector 306 such as a Luer connector allows a syringe or other device to be fluidly coupled to the device to pre-fill the device with the therapeutic agent, or to fill and deliver the drug during use. A lumen in each loop forms a drug reservoir similar to those previously described above. Each loop may have a foam contact element disposed thereover, or as illustrated, the loops may be foamless. Each loop has a plurality of pores (not illustrated) to allow the therapeutic agent to be released therefrom. An optional stiffening member (not illustrated) such as a wire may be disposed in each loop in order to help maintain shape and patency of the loop. In alternative embodiments, the drug reservoir may include an inflatable inner chamber that can help push the outer surface of the loops against the target tissue, and that will help push the therapeutic agent out of the reservoir. FIG. 11 shows a cross-section of a porous drug reservoir 310 with an inflatable inner chamber 312 for facilitating release of the therapeutic agent 314 through the pores of the reservoir. In addition to loops, the delivery device may have a single porous balloon, an array of balloon fingers, or corkscrew-like elements for delivering drug to the target tissue.

Figure 12A:
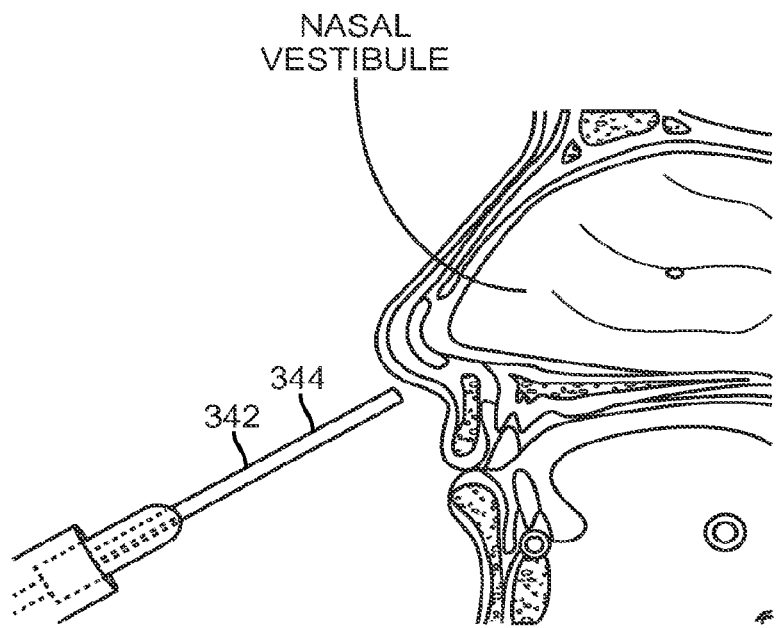
FIGS. 12A-12B illustrate an exemplary method of delivering a therapeutic agent to the nasal cavity.
Figure 12B:
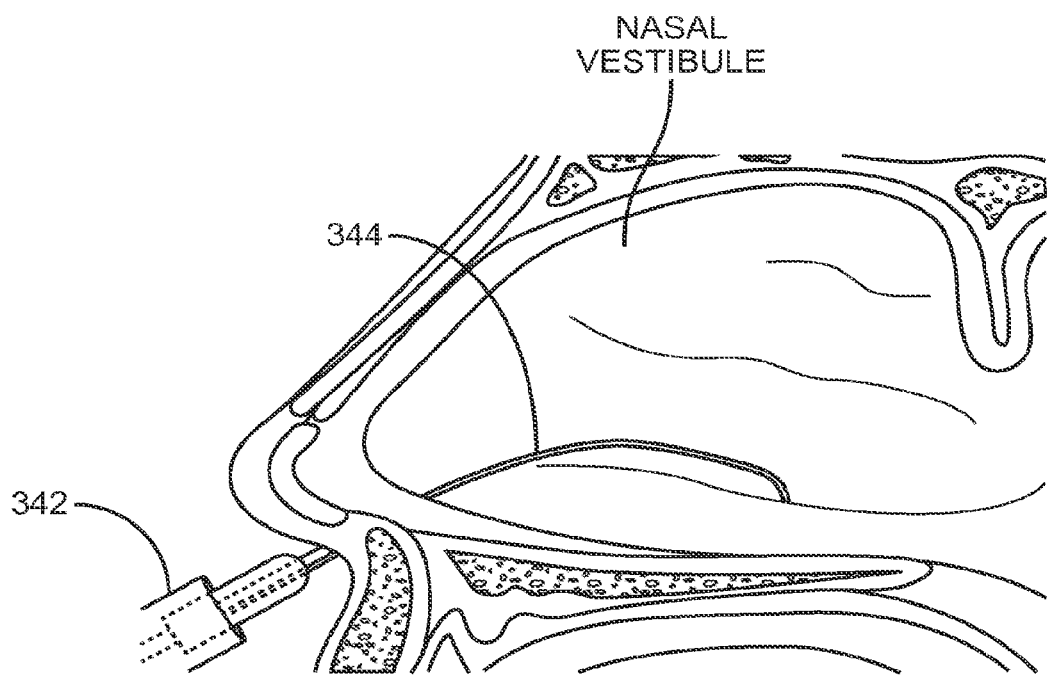

FIGS. 12A-12B illustrate an exemplary method of advancing a drug delivery device having looped elements into the nasal cavity. The drug delivery device in FIGS. 12A-12B only has a single looped element, but one of skill in the art will appreciate that it may also have multiple looped elements, similar to the embodiment in FIG. 10. The loop element 344 having the porous drug reservoir is retracted into and constrained by sheath 342 for minimum profile that can be advanced into the nasal cavity via a nostril. Once the device has been introduced into the nasal cavity, the sheath may be retracted (or the loop may be advanced) so that the loop becomes unconstrained and it expands into its full shape as seen in FIG. 12B. The therapeutic agent may then be delivered from the loop into the target tissue. Once the drug has been delivered, the loop may be resheathed, and the device removed from the patient's nose.

Figure 13A:
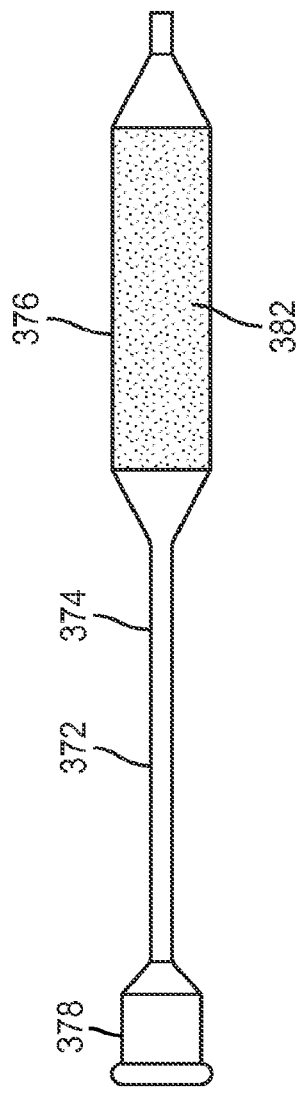
FIGS. 13A-13C illustrate a porous balloon for delivery of a therapeutic agent to the nasal cavity.
Figure 13B:
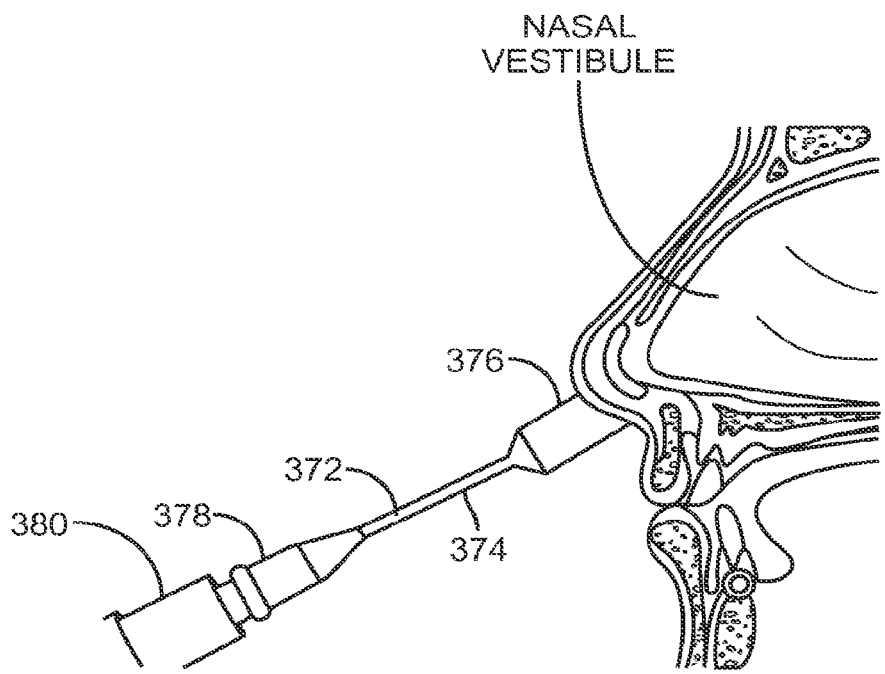
Figure 13C:
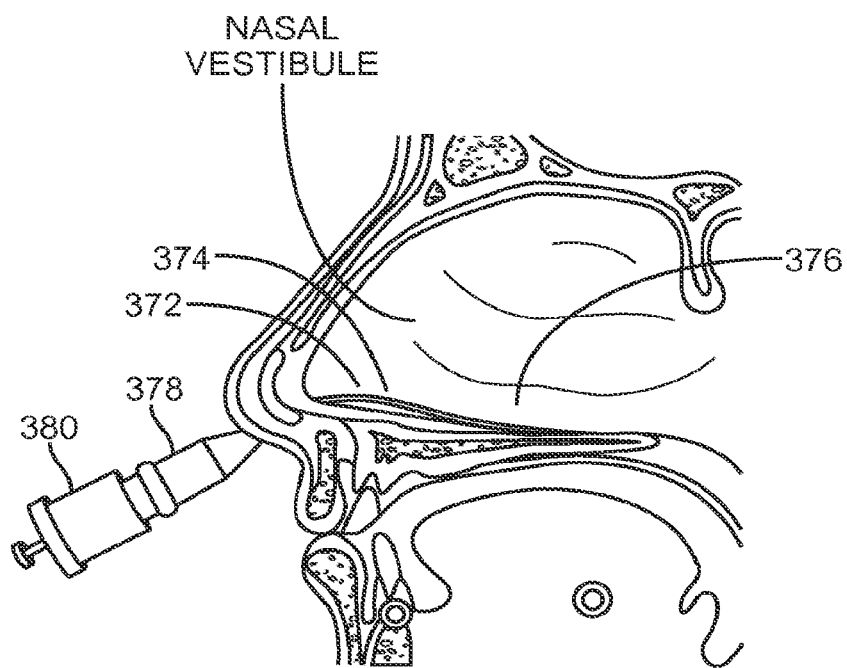
Figure 13D:
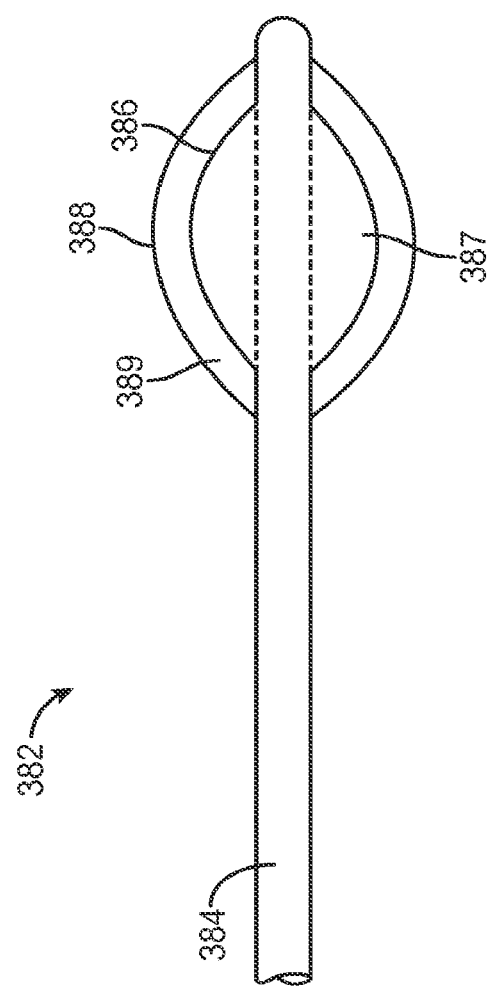
FIG. 13D illustrates another balloon embodiment for delivery of a therapeutic agent.

FIGS. 13A-13C illustrate use of a porous balloon to deliver a therapeutic agent to the nasal cavity. A catheter 372 includes an elongate flexible shaft 374 having a porous balloon 376 disposed at the distal end of the shaft 374. The balloon 376 includes a plurality of micropores 382 in the balloon wall which allow a therapeutic agent to be delivered therefrom when the balloon is pressurized. An optional foam contact element (not illustrated) similar to those previously disclosed above may be disposed over the porous balloon 376. A connector 378, such as a Luer connector is coupled to a proximal end of the elongate shaft 374 in order to allow a syringe or other component to be fluidly coupled to the catheter 372. In FIG. 13B, the catheter 372 is advanced toward the patient's nasal cavity, and the distal tip is inserted into the nostril. An optional valve member 380 may be coupled to connector 378 to prevent backflow of the therapeutic agent. In FIG. 13C, the balloon 376 is advanced into a desired portion of the nasal cavity, and a syringe or other reservoir device (not illustrated) is coupled to valve 380, and the therapeutic agent is then transferred from the syringe or reservoir to the porous balloon 376. As the balloon inflates, the therapeutic agent passes through the micropores 382 in the balloon wall, and the therapeutic agent is then delivered to the desired target tissue. In one embodiment, the volume of the balloon is about 0.3 ml, and it is filled multiple times during placement and use in order to deliver 1 ml of drug solution (such as a toxin like botulinum toxin) to one side, or both sides of the nose. Placement of the balloon may be adjusted between fills so that the drug is delivered to different areas of the anatomy. Also, in some embodiments, multiple balloons may be inserted into the nasal cavity for simultaneous delivery of a larger quantity of drug to a larger surface area. A final filling of the balloon with water or a saline solution may be used to flush the remaining drug solution out of the balloon, and the device may be removed from the patient's nose.

In an alternative embodiment as seen in FIG. 13D, the delivery system 382 includes an elongate shaft 384 having inner balloon 386 and an outer balloon 388 or outer spongy layer 388 disposed near the distal portion of the elongate shaft 384. The outer balloon 388 may be disposed over the inner balloon 386 or the spongy outer layer 388 may be disposed on top of the inner balloon 386. In this embodiment, the inner balloon 386 does not act as the drug reservoir and is not inflated for the purpose of pushing drug out of the outer balloon or spongy layer. Instead, the space 387 of the inner balloon 386 is inflated with a fluid such as a gas (e.g. air or nitrogen) or saline in order to reduce the remaining volume of the nasal cavity. Thus, the small remaining volume of the nasal cavity can easily be filled with the inflated outer balloon or spongy layer 388. Therefore the expanded volume of the inner balloon is preferably greater than the expanded volume of the outer balloon or spongy layer. Because the volume of the nasal cavity has been reduced, the therapeutic agent may be delivered in a higher concentration and lower volume and it will be more precisely delivered to a smaller volume. Using a higher concentration achieves a better therapeutic effect with a smaller and less dangerous amount of the drug required. The therapeutic agent may be a toxin such as those described in this specification or it may be other drugs including non-toxins. The therapeutic agent may be delivered via a lumen in shaft 384 to the space 389 between the inner and outer balloons and the outer balloon may be porous to allow the drug to be delivered to the tissue, or the drug may be delivered via a lumen in the shaft 384 to exit ports (not illustrated) on the shaft 384. In other embodiments, the drug may be held in the spongy layer 388 and delivered to the tissue upon contact thereagainst.

Figure 14A:
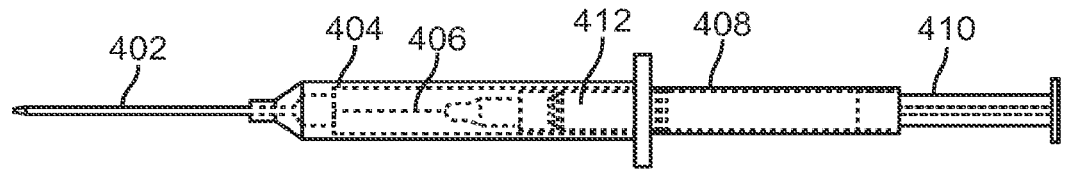
FIGS. 14A-14C illustrate an embodiment of a delivery device having a tissue penetrating needle.
Figure 14B:
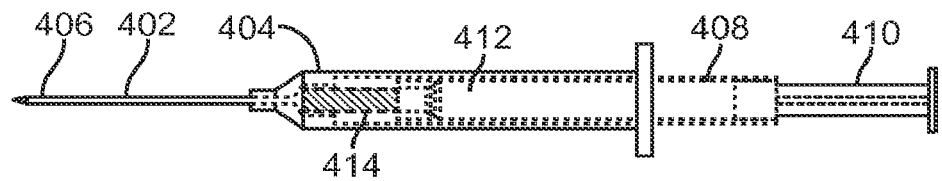
Figure 14C:
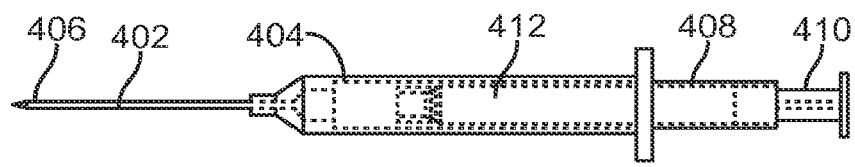

FIGS. 14A-14C illustrate an exemplary embodiment of a drug delivery device having a tissue penetrating needle that may be used to deliver a therapeutic agent to nasal cavity. The delivery device includes an outer syringe barrel 404 and an inner syringe barrel 408. In preferred embodiments, the inner syringe barrel is a 3 ml syringe holding a 1 ml volume of therapeutic agent, and the outer syringe barrel is a 5 ml syringe, although this is not intended to be limiting. An elongate flexible sleeve 402 is coupled to the distal end of the outer syringe barrel 404, and a tissue penetrating needle 406 is coupled to the distal end of the inner syringe barrel 408. The inner syringe barrel 408 is slidably disposed in the outer syringe barrel 404. The inner syringe barrel serves as a drug reservoir 412 for holding a therapeutic agent. Actuation of plunger 410 by distal advancement forces the therapeutic agent out of the reservoir 412 and through needle 406. In preferred embodiments, the inner syringe barrel 408 is disposed in a retracted position relative to the outer syringe barrel 404 such that needle 406 remains in outer syringe barrel 404, unexposed, as illustrated in FIG. 14A. Distal advancement of the inner syringe barrel relative to the outer syringe barrel advances the needle distally through sleeve 402 until the distal tissue piercing tip of the needle 406 is exposed, as seen in FIG. 14B. An optional spring 414 may be disposed between a distal end of the inner syringe barrel and a distal portion of the outer syringe barrel. This spring 414 is biased to retract the inner syringe barrel away from the outer syringe barrel, thus the tissue piercing needle will be biased to remain unexposed in the outer syringe barrel. Once the needle is exposed, the plunger 410 may be distally advanced to force the therapeutic agent out of the reservoir 412 and out the needle 406 into the target tissue.

The device in FIGS. 14A-14C may be used to inject a therapeutic agent such as a toxin like botulinum toxin into specific regions of tissue such as the turbinates. One injection, or multiple injections may be used. Also, because the needle is covered during initial delivery, this may help reduce patient anxiety associated with seeing a needle. Also, the sleeve is flexible, and therefore can navigate the nasal anatomy easier than a more rigid needle. And once the device has been positioned in a desired area of the nasal cavity, the sleeve will act as a guide to help the needle smoothly advance through the anatomy to the target. This may help reduce patient discomfort and also reduce trauma to the tissue. Also, the amount of needle that is exposed from the sleeve may be controlled or fixed, thereby controlling the penetration depth which helps to prevent overly deep delivery of the therapeutic agent. In some embodiments, an indicator mechanism such as tactile, visual, or auditory mechanisms allow the operator to know when the needle is exposed and how far it is exposed, and how much drug is delivered. An anesthetic such as Lidocaine may also be used to help alleviate patient discomfort. The Lidocaine may be injected separately, or it may be mixed with some compatible therapeutic agents and injected simultaneously.

Figure 15A:
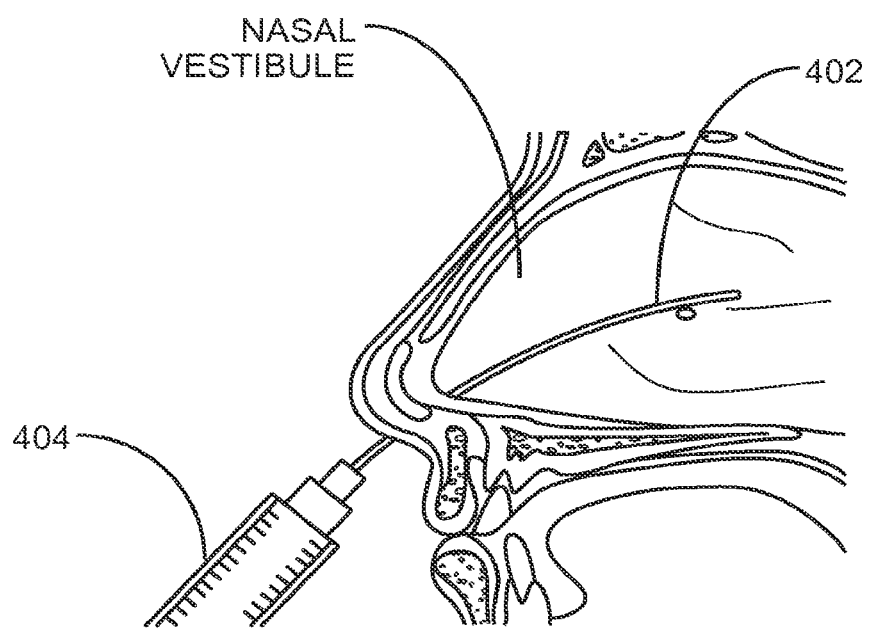
FIGS. 15A-15B illustrate use of the device in FIGS. 14A-14C to deliver a therapeutic agent to the nasal cavity.
Figure 15B:
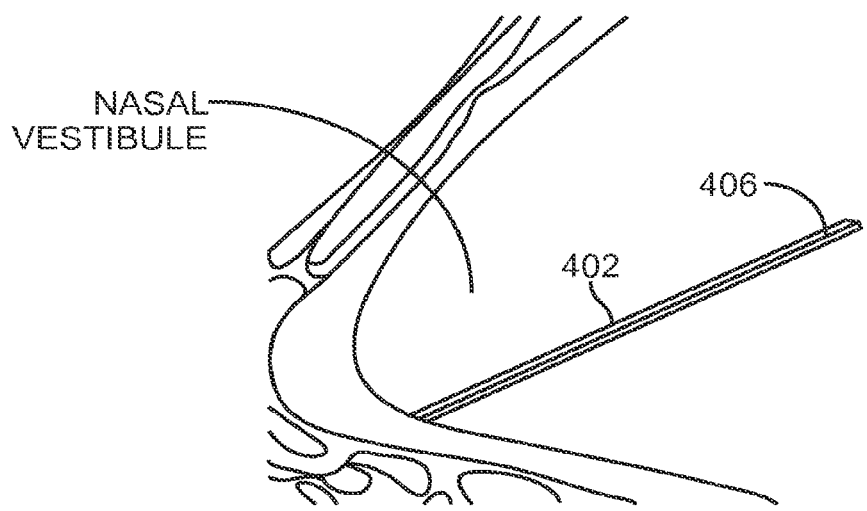

FIGS. 15A-15B illustrate exemplary usage of the device in FIGS. 14A-14C. The sleeve 402 is advanced through a nostril into the nasal cavity as seen in FIG. 15A. Advancement of the sleeve is performed while the needle is retracted into the outer syringe barrel 404. Once the sleeve has been delivered to the target treatment site, the needle 406 is advanced distally so that it is exposed from the sleeve 402 as illustrated in FIG. 15B. The needle may then be advanced into the tissue and the therapeutic agent delivered therefrom.

Figure 16A:
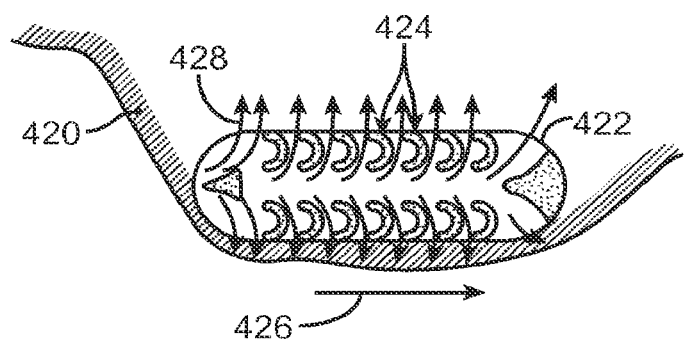
FIGS. 16A-16C illustrate use of a nasal patch to deliver a therapeutic agent to the nasal cavity.
Figure 16B:
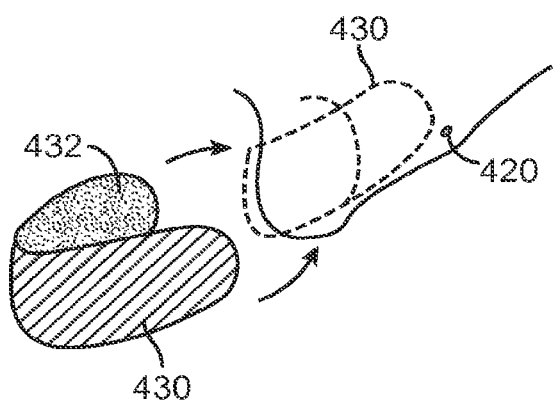
Figure 16C:
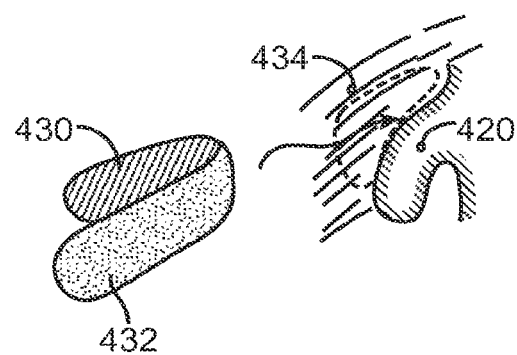

FIGS. 16A-16C illustrate the use of a patch to delivery a therapeutic agent to a nasal cavity. The patch 422 may be similar to transdermal drug delivery patches, and it may include a porous reservoir for holding and delivering the therapeutic agent 428, and that is joined to a flexible adhesive structure for temporary attachment to the target tissue, such as a nasal turbinate 420. The adhesive areas 424 of the patch 422 may be arranged to ensure that the patch will stick to the tissue (e.g. mucosa tissue) with or without requiring removal of mucosa prior to application of the patch. Additionally, the adhesive areas 424 may be arranged in order to work in concert with the cilial transport mechanism of the underlying mucosa, as indicated by arrow 426. Cilial transport will be temporarily interrupted in the adhesive locations yet continue to function in other areas. This can act to slow the cilial transport of the drug solution and increase its residence time, or steer the drug solution away to affect a broader area. The patch 430 may be flexible such that it can be folded and the adhesive side 432 affixed to the anterior surface of a turbinate 420 as seen in FIG. 16B, or the patch 430 may be folded in the opposite direction to be placed in the meatus between a turbinate 420 and the nasal septum or another turbinate as seen in FIG. 16C.

Therapeutic agents such as toxins like botulinum toxin may also be spayed on or painted on to a target tissue. Spray applicators may use pressurized gas to spray the drug onto the tissue. Droplet size, viscosity may be controlled, and a broad area may be easily treated with the therapeutic agent. High pressure spraying may also be used to help ensure that the therapeutic agent penetrates the mucus blanket covering the mucosa. In other embodiments, lower pressure may be used to spray a more viscous solution of the therapeutic agent onto the target tissue in order to increase its residence time for greater drug penetration into the tissue. While spray methods are promising, in certain situations, the sprays can be hard to control which is undesirable when delivering a toxin. Additional controls may be implemented to help ensure proper delivery of the toxin. For example, delivery may be coordinated with the patient's breathing such that drug delivery only occurs when the patient exhales. Exhalation produces a strong airflow out of the lungs and closes the soft palate to seal the nasal cavity from the mouth and inferior pharynx. This prevents toxins from entering the lungs. Additionally, multiple smaller doses may be administered in order to limit the danger of one large does. Also, viscosity and droplet size may be controlled to increase residence time and help prevent aspiration into unwanted areas.

Figure 17:
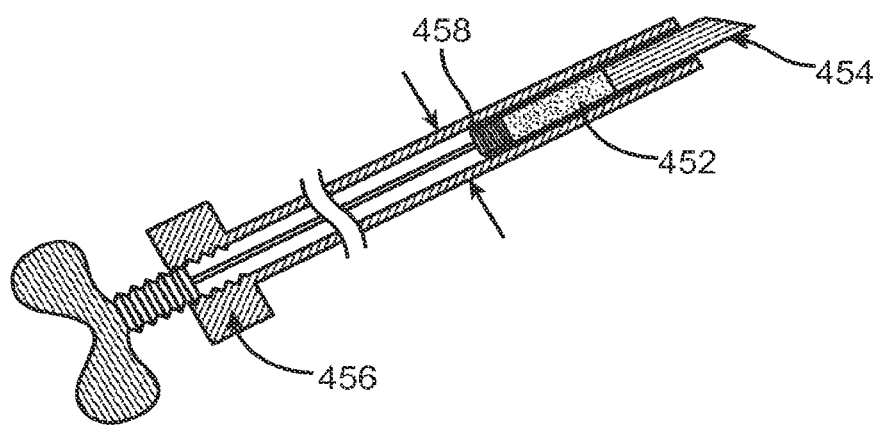
FIG. 17 illustrates a paint on device for delivering a therapeutic agent.
Figure 18:
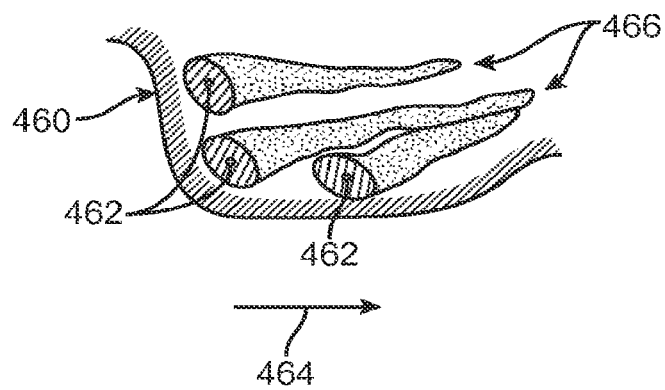
FIG. 18 illustrates cilial transport of a therapeutic agent.

Paint applicators may also be used to deliver a therapeutic agent. They allow control over drug application, and also allow broad coverage. FIG. 17 illustrates an exemplary embodiment of a paint on applicator. The applicator is similar to a felt tipped pen. It includes a drug reservoir 452 and a wicking tip 454. Actuation of pressure mechanism 456 moves plunger 458 thereby forcing drug out of the reservoir. The wicking tip 454 may be used to paint on the therapeutic agent to a desired target tissue. For example, in FIG. 18, three regions 462 are initially painted on the turbinate 460 using the device of FIG. 17. Cilial transport 464 causes the drug to flow thereby further spreading the drug in the nasal cavity.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for delivering a therapeutic agent to a nasopharyngeal mucosa tissue, said method comprising:
- inserting a porous pad in a collapsed configuration into a nasal cavity, the porous pad extending around an expandable member and a drug reservoir containing a therapeutic agent, wherein the porous pad is substantially dry during the insertion;
- with the porous pad inserted in the nasal cavity, expanding the expandable member and applying pressure to the drug reservoir thereby pushing the therapeutic agent out therefrom to wet the porous pad with the therapeutic agent thereby expanding the porous pad into an expanded configuration that engages the mucosa tissue; and
- delivering the therapeutic agent from the porous pad to the mucosa tissue.

2. The method of claim 1, wherein a sheath remains disposed over the porous pad during the insertion, constraining the porous pad in the collapsed configuration.

3. The method of claim 1, wherein wetting the porous pad comprises opening at least one valve fluidly coupled with the drug reservoir to allow the therapeutic agent to flow therefrom to the porous pad.

4. The method of claim 1, wherein applying pressure comprises inflating an expandable member against the drug reservoir.

5. The method of claim 1, further comprising removing a constraining sheath from the porous pad, thereby allowing the porous pad to expand into the expanded configuration.

6. The method of claim 1, wherein the therapeutic agent comprises a toxin configured to inhibit mucus secretions.

7. The method of claim 6, wherein the toxin comprises botulinum toxin.

8. The method of claim 1, further comprising reducing or eliminating symptoms associated with rhinitis.

9. The method of claim 1, wherein the expandable member comprises an expandable foam layer.

10. The method of claim 9, wherein the expandable foam layer comprises hydrophobic foam to inhibit absorption of the therapeutic agent therein.

11. The method of claim 9, wherein the expandable foam layer is self-expanding.

12. The method of claim 9, wherein the expandable foam layer comprises a plurality of pores in communication with the drug reservoir, wherein upon applying pressure to the drug reservoir, the therapeutic agent flows from the drug reservoir through the pores to the porous pad.

13. The method of claim 1, wherein the expandable member is disposed between the drug reservoir and the porous pad.

14. The method of claim 13, wherein the drug reservoir is fluidly isolated from the expandable member.

15. The method of claim 1, wherein the drug reservoir is disposed between the expandable member and the porous pad.

16. The method of claim 1, wherein the expandable member resists absorption of the therapeutic agent.

17. The method of claim 1, wherein the drug reservoir comprises a plurality of drug reservoirs.

18. The method of claim 17, wherein the plurality of drug reservoirs are isolated from one another by a plurality of valves.

19. A method for delivering a therapeutic agent to a nasopharyngeal mucosa tissue, said method comprising:
- inserting a porous pad in a collapsed configuration into a nasal cavity, the porous pad extending around an expandable member and being in fluid communication with a drug reservoir containing a therapeutic agent, wherein the porous pad is substantially dry during the insertion;
- with the porous pad inserted in the nasal cavity, expanding the expandable member to engage the porous pad against the mucosa tissue;
- wetting the porous pad with the therapeutic agent from the drug reservoir; and
- delivering the therapeutic agent from the porous pad to the mucosa tissue.

20. The method of claim 19, wherein a sheath remains disposed over the porous pad during the insertion, constraining the porous pad in the collapsed configuration.

21. The method of claim 19, wherein wetting the porous pad comprises opening at least one valve fluidly coupled with the drug reservoir to allow the therapeutic agent to flow therefrom to the porous pad.

22. The method of claim 19, further comprising removing a constraining sheath from the porous pad, thereby allowing the porous pad to expand into the expanded configuration.

23. The method of claim 19, wherein the therapeutic agent comprises a toxin configured to inhibit mucus secretions.

24. The method of claim 23, wherein the toxin comprises botulinum toxin.

25. The method of claim 19, further comprising reducing or eliminating symptoms associated with rhinitis.

26. The method of claim 19, wherein the expandable member comprises an expandable foam layer.

27. The method of claim 26, wherein the expandable foam layer comprises hydrophobic foam to inhibit absorption of the therapeutic agent therein.

28. The method of claim 26, wherein the expandable foam layer is self-expanding.

29. The method of claim 19, wherein the expandable member is disposed between the drug reservoir and the porous pad.

30. The method of claim 29, wherein the drug reservoir is fluidly isolated from the expandable member.

31. The method of claim 19, wherein the drug reservoir is disposed between the expandable member and the porous pad.

32. The method of claim 19, wherein the expandable member resists absorption of the therapeutic agent.

33. The method of claim 19, wherein the drug reservoir comprises a plurality of drug reservoirs.

34. The method of claim 33, wherein the plurality of drug reservoirs are isolated from one another by a plurality of valves.

35. The method of claim 19, wherein the therapeutic agent is infused into the porous pad through an infusion lumen.

36. The method of claim 35, wherein the expandable member is expanded with fluid introduced from an inflation lumen separate from the infusion lumen.

* * * * *